United States Patent
Aze et al.

(10) Patent No.: US 7,458,253 B2
(45) Date of Patent: Dec. 2, 2008

(54) METHOD FOR EVALUATING FIXING MEMBER AND FIXING BELT AND THERMAL FIXING ROLLER

(75) Inventors: Norihiko Aze, Ohta-ku (JP); Kyoichi Ashikawa, Ohta-ku (JP); Kohji Kamiya, Ohta-ku (JP); Minoru Matsuo, Ohta-ku (JP); Takayuki Yoshii, Ohta-ku (JP); Nozomu Takahata, Ohta-ku (JP)

(73) Assignee: Ricoh Company, Ltd., Tokyo (JP)

( * ) Notice: Subject to any disclaimer, the term of this patent is extended or adjusted under 35 U.S.C. 154(b) by 383 days.

(21) Appl. No.: 11/344,000

(22) Filed: Feb. 1, 2006

(65) Prior Publication Data

US 2006/0120778 A1    Jun. 8, 2006

Related U.S. Application Data

(63) Continuation of application No. 10/664,920, filed on Sep. 22, 2003, now Pat. No. 7,024,923, which is a continuation-in-part of application No. 10/394,227, filed on Mar. 24, 2003, now abandoned.

(30) Foreign Application Priority Data

Mar. 22, 2002  (JP) .............................. 2002-081741
Jul. 23, 2003   (JP) .............................. 2003-200442

(51) Int. Cl.
    *G01N 3/48*    (2006.01)

(52) U.S. Cl. ............................ 73/81; 73/865.9; 73/866; 399/302; 399/308; 399/297

(58) Field of Classification Search .................... 73/81, 73/865.9, 866; 399/302, 308, 297
See application file for complete search history.

(56) References Cited

U.S. PATENT DOCUMENTS

| 3,194,061 | A | 7/1965 | Sorenson et al. |
| 6,103,851 | A * | 8/2000 | Roser et al. .................... 528/77 |
| 6,175,712 | B1 * | 1/2001 | Masuda et al. .............. 399/302 |
| 6,314,798 | B2 | 11/2001 | Nomura et al. |

(Continued)

FOREIGN PATENT DOCUMENTS

JP        9-44009        2/1997

(Continued)

OTHER PUBLICATIONS

U.S. Appl. No. 11/613,039, filed Dec. 19, 2006, Aze et al.

*Primary Examiner*—Hezron E. Williams
*Assistant Examiner*—Gunnar J Gissel
(74) *Attorney, Agent, or Firm*—Oblon, Spivak, McClelland, Maier & Neustadt, P.C.

(57) ABSTRACT

In a method for evaluating a fixing member to fix a toner having a surface layer, a hardness test is carried out by applying a pressure deformation from the surface side of the fixing member, and when a deformation of the surface layer by the pressure deformation is within an elastic range, the fixing member is regarded as a standard product.

2 Claims, 19 Drawing Sheets

U.S. PATENT DOCUMENTS

| | | |
|---|---|---|
| 6,538,365 B2 | 3/2003 | Nasu et al. |
| 6,555,210 B1 | 4/2003 | Masuda et al. |
| 6,618,573 B2 | 9/2003 | Ishikawa et al. |
| 6,650,471 B2 | 11/2003 | Doi |
| 6,801,372 B2 | 10/2004 | Doi |
| 6,861,124 B2 | 3/2005 | Kamiya et al. |
| 7,024,923 B2 * | 4/2006 | Aze et al. ................ 73/81 |
| 2003/0169323 A1 * | 9/2003 | Fukuda et al. ............ 347/103 |
| 2006/0120778 A1 * | 6/2006 | Aze et al. ................ 399/328 |

FOREIGN PATENT DOCUMENTS

| | | |
|---|---|---|
| JP | 9-281835 | 10/1997 |
| JP | 10-198201 | 7/1998 |
| JP | 11-295968 | 10/1999 |
| JP | 2000-47496 | 2/2000 |
| JP | 2001-125298 | 5/2001 |
| JP | 2001-215767 | 8/2001 |

* cited by examiner

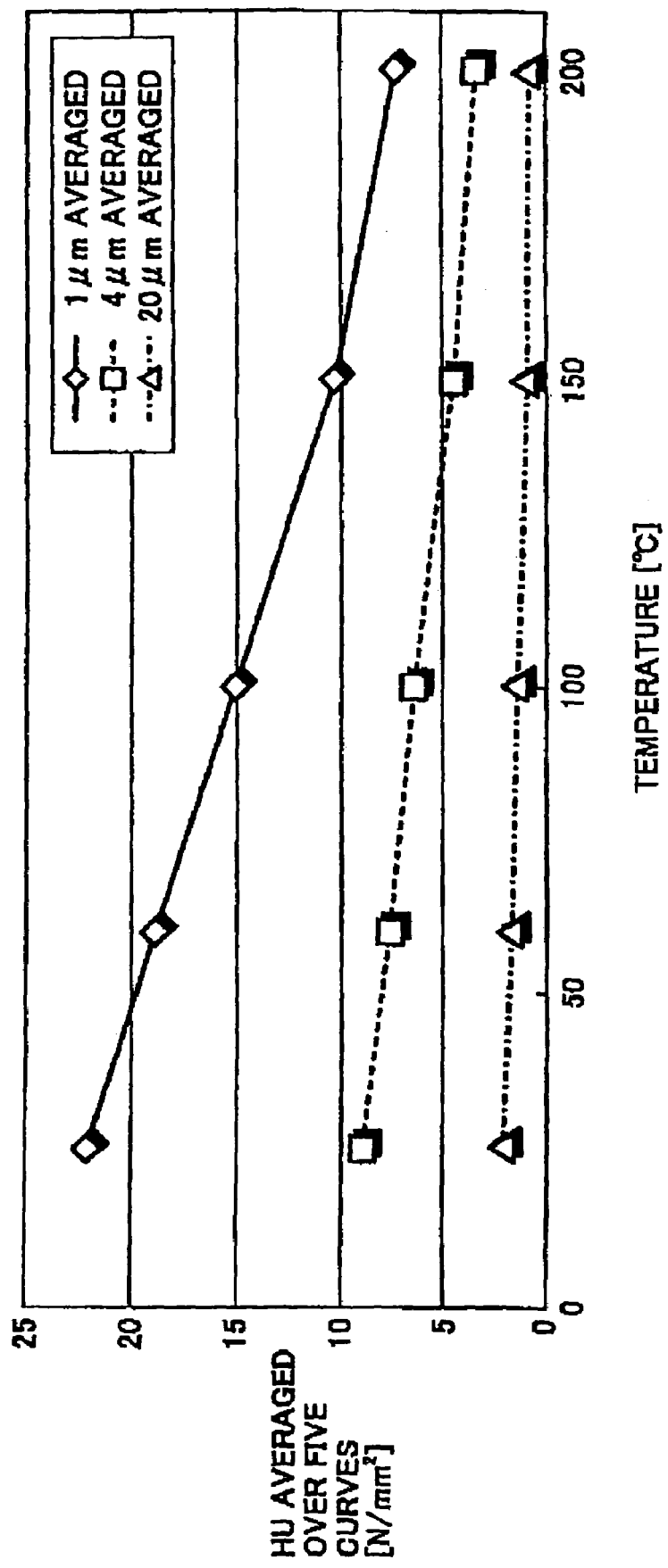
FIG.11 RELATIONSHIP BETWEEN INDENTATION DEPTH/TEMPERATURE AND UNIVERSAL HARDNESS (AVERAGE OF FIVE VALUES)

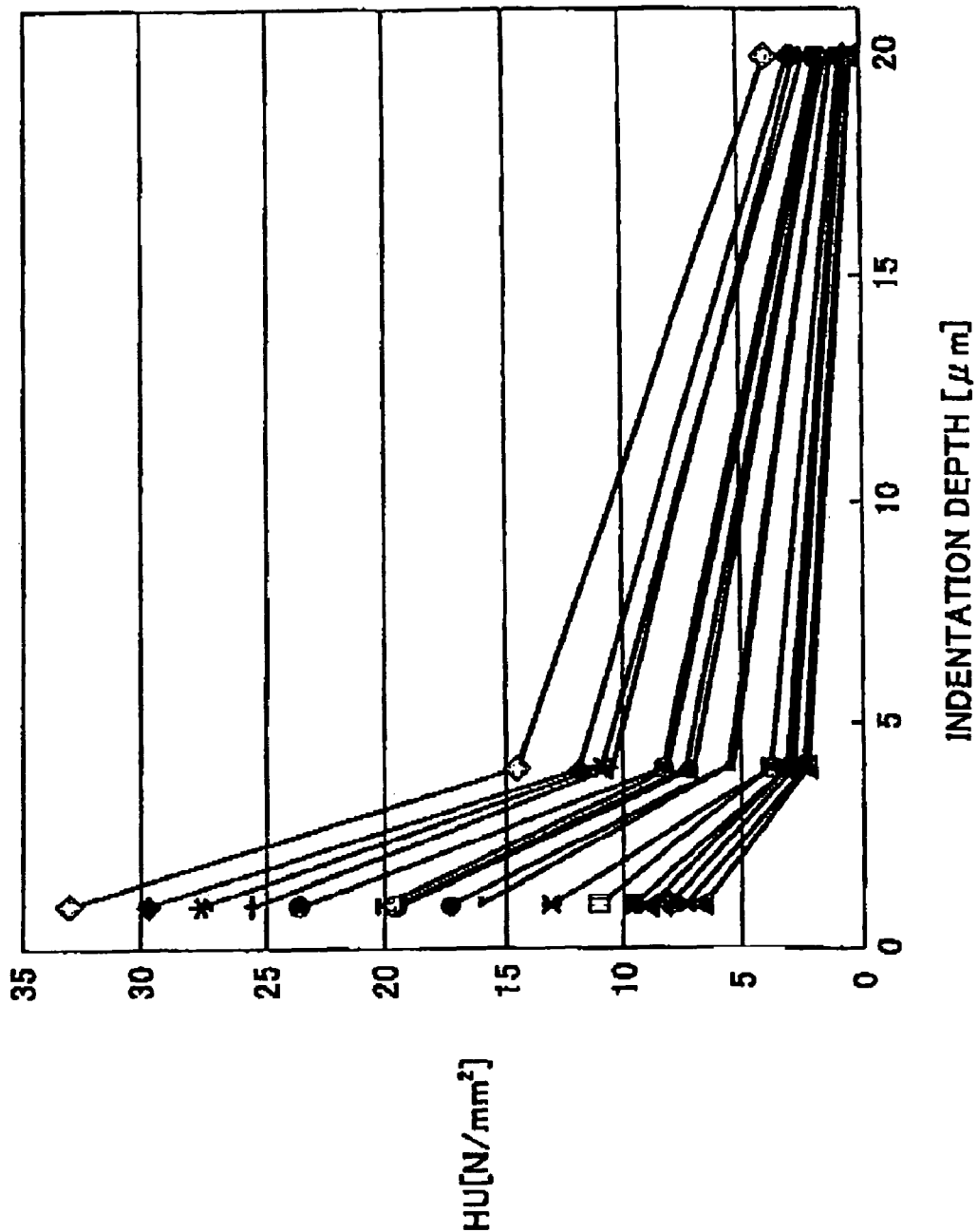

METHOD FOR EVALUATING FIXING MEMBER AND FIXING BELT AND THERMAL FIXING ROLLER

BACKGROUND OF THIS INVENTION

1. Field of the Invention

The present invention relates to a method for evaluating a fixing member, more specifically, to a method for evaluating a fixing belt and/or a thermal fixing roller used in an electrophotographic apparatus or the like, and also relates to such a fixing belt and such a thermal fixing roller.

2. Description of the Prior Art

FIG. 21 is a schematic sectional drawing for explaining an image forming process in an electrophotographic apparatus. The schematic drawing represents a process of forming a monochromatic image. However, in the process of forming a full color image, developing units for four different colors, i.e., red (magenta), blue (cyan), yellow (yellow) and black (black) as well as a mechanism for mixing or superimposing the four color images are employed.

The electrophotographic apparatus (for instance, a copy machine or a laser printer) is equipped with a rotary photoconductor drum 1. A photosensitive layer on the photoconductor drum 1 is uniformly charged by an electrostatic charging unit 2, and then exposed by a laser beam 3 emitted from a laser-scanning unit. Moreover, in a developing device 4 of the electro-photographic apparatus, an electrostatic latent image, which is formed on the photoconductor drum 1, is developed by a toner, and a toner image is produced. Consequentially, the toner image is transferred to a recording paper 6 with the aid of a transfer roller 5. Furthermore, reference numeral 7 denotes a power supply unit (power pack) for applying voltage, reference numeral 8 denotes a surface electrometer for measuring a surface potential of the photoconductor drum 1, and reference numeral 9 denotes a cleaning unit for cleaning the surface of the photoconductor drum 1.

In the following, a thermal fixing apparatus used for thermally fixing the toner image transformed onto the recording paper 6 will be described. Traditionally, it is known that a roller-type thermal fixing apparatus 10, as shown at the upper left in FIG. 21, is used to thermally fix a toner for a monochromatic image (only back toner). Such a thermal fixing apparatus 10 is equipped with a thermal fixing roller 11 and a press roller 12 which are disposed in parallel to each other in order to put or sandwich a recording paper 6 between the thermal fixing roller 11 and the press roller 12. The thermal fixing roller 11 includes a hollow cylindrical core body made of aluminum or the like, and an adhesion-preventing layer for preventing toner from adhering is coated onto an outer circumferential surface of the core body, where the layer is made of fluorocarbon resin or the like. Moreover, heaters as a halogen lamp or the like (not shown) are disposed parallel to the center line of the hollow space inside the core body of the thermal fixing roller 11, thereby enabling the roller main body to be heated from the inside thereof by the radiation emitted from the heater. The movement of the recording paper 6 between the thermal fixing roller 11 and the press roller 12 causes the toner on the recording paper 6 to be softened (molten) due to the heat from the thermal fixing roller 11, so that the toner is fixed onto the recording paper 6 with the aid of the press roller 12.

The above-described thermal fixing roller having a fluorocarbon resin layer is excellent as for the toner separation ability (releaseablity), but it is inferior as for both the flexibility and elasticity, so that such a fixing roller is not be able to be suitable for using in a full color copying machine and/or a full color laser printer, which requires a glossy printing surface. Four types of color toners are conventionally used in the full color copying machine or the laser printer of the glossy image. These four color toners have to be mixed in a molten state when the color image is fixed. In other words, the four color toners are prepared to be easily molten by lowering a melting point, and several color toners must be uniformly mixed in the molten state in which the toners are wrapped on the surface of the thermal fixing roller. Therefore, it is particularly important for the surface of the thermal fixing roller to have an appropriate flexibility and elasticity. (Reference to Japanese patent laid-open Hei10-198201)

On the other hand, it is also known that a belt-type thermal fixing apparatus 15, as shown at the lower left in FIG. 21. In the thermal fixing apparatus 15, a layer-shaped fixing belt 18 is wounded between a fixing roller 16 and a heating roller 17, and further a press roller 19 is disposed in parallel to the fixing roller 16. In this arrangement, the heating roller 17 heats the fixing belt 18, and then a recording paper 6 passes through a contact surface between the fixing roller 16 and the press roller 19. The recording paper 6 is heated in the course of the passage, so that a toner image is transferred onto the recording paper 6 and then fixed thereon.

The above-mentioned fixing belt 18 has a gummy elastic layer made of silicone gum, fluorocarbon gum or the like on the surface. Such an elastic layer provides an excellent flexibility and elasticity. However, the toner separation ability is lacked, so that the toner-offset phenomenon often occurs.

In recent years, taking these facts into account, a fixing belt and a thermal fixing roller have been proposed, which are formed by coating a gummy elastic layer on a base element and further by coating a toner separation material of fluorocarbon resin or the like on the gummy elastic layer.

However, the fixing belt or the thermal fig roller in the prior art in which such a separation layer made of as fluorocarbon resin is coated onto the gummy elastic layer, causes important properties required for the surface of the fixing belt and the thermal fixing roller, i.e., the flexibility and the elasticity, to be deteriorated.

The fixation of the toner with a fixing belt or a thermal icing roller having inadequate flexibility and elasticity provides either a matt pattern in an image (unevenness in the image intensity). Moreover, when an image is fixed on an OHP sheet, an opaque pattern in an image on an OHP sheet is caused.

Such a problem no longer arises, if it may be ascertained with case whether or not a fixing belt or a thermal fixing roller has an appropriate flexibility and elasticity. Unfortunately, there is no conventional method for synthetically evaluating the hardness of the separation layer, taking into account the influence of the base element and the elastic layer thereon.

SUMMARY OF THE INVENTION

Accordingly, it is an object of the present invention to provide a method for evaluating a fixing member, in which excellence in the toner separation ability, the flexibility and elasticity can be easily evaluated, and it is another object of the present invention to provide a fixing belt and a thermal fixing roller which have an excellent toner separation ability, flexibility, and elasticity.

In order to attain the above-mentioned objects, a first aspect of the present invention is to provide a method for evaluating a fixing member. In the method, the universal hardness test is carried out for a fixing member used to fix a toner having a surface layer by applying a pressure deformation from the surface side of the filing member at a room temperature, and when the deformation of the surface layer is within an elastic range, the fixing member is regarded as a standard product.

A second aspect of the present invention is to provide a method for evaluating a fixing member used to fix a toner. In the method, the universal hardness test is carried out for an indentation depth of 1 μm from the surface side of the fixing member at a room temperature, and when the universal hardness HU for the indentation depth of 1 μm satisfies a relation, HU≦30 [N/mm²], the fixing member is regarded as a standard product.

In order to attain the above-mentioned objects, a third aspect of the present is to evaluate the fixing member used to fix the toner in such a manner that the universal hardness test is carried out for each of indentation depths of 1 μm to 4 μm from the surface side of the fixing member, when the universal hardness HU for the indentation depth of 1 μm satisfies the relation, HU≦30 [N/mm²], and at the same time, when the universal hardness HU for the indentation depth of 4 μm satisfies a relation HU≦12 [N/mm²], the fixing member is regarded as a standard product.

The present inventors intensively carried out investigations on a fixation of toner images developed on a paper, an OHP film or the like without generating unevenness of the image. The result obtained by the intense investigations revels that a surface hardness of the fixing member can be optimally evaluated by utilizing the universal hardness HU, which is specified in the German Industrial Standard, DIN 50359-1 (this standard is capable of describing properties of materials in a much more detailed manner).

In particularly, by measuring the universal hardness HU for each of the indentation depths of 1 μm to 4 μm from the surface side of the fixing member, for example, if the relation HU≦30 [N/mm²] is satisfied for the indentation depth of 1 μm and at the same time, if the relation HU≦12 [N/mm²] is satisfied for the indentation depth of 4 μm, the fixing member can be regarded as a standard product.

In the third aspect of the present invention, the universal hardness test is carried out at a test environment temperature of 25° C.

The universal hardness test can also be carried out at a test environment temperature of 200° C. as a fourth aspect of the present invention. In other words, the fourth feature of the present invention is to evaluate the fixing member used to fix the toner in such a manner that the universal hardness test is carried out at the test environment temperature of 200° C. for each of indentation depths of 1 μm to 4 μm from the surface side of the fixing member, when the universal hardness HU for the indentation depth of 1 μm satisfies the relation, HU≦10 [N/mm²], and at the same time, when the universal hardness HU for the indentation depth of 4 μm satisfies the relation HU≦4 [N/mm²], the fixing member is regarded as a standard product.

In the third and the fourth aspects of the above-mentioned fixing member, it is preferable that a contact angle when a water-drop is contacted onto the surface of the fixing member is more than 95 degrees.

At this point, the test environment temperature of 25° C. is suited to a room temperature, and the test, environment temperature of 200° C. is suited to a running temperature in which the fixing member is exposed at the time of fixing the toner. An upper limit of the universal hardness HU at the indentation depth of 1 μm from the surface of the fixing member is respectively set to 30 [N/mm²] when the test environment temperature is 25° C. and 10 [N/mm²] when the test environment temperature is 200° C. The universal hardness HU under the room temperature is also three times of the universal hardness under the running temperature. A fifth aspect of the present invention is guided by this condition.

The fifth aspect of the present invention is to evaluate the fixing member used to fix the toner in such a manner that the universal hardness test is carried out respectively at the room temperature and the running temperature of the fixing belt for each of the indentation depths of 1 μm to 4 μm from the surface side of the fitting member, when the each of the universal hardness HU at the same depth from the surface of the fixing belt is compared, if the universal hardness HU under the room temperature is three times of the universal hardness HU under the running temperature, the fixing belt is able to be regarded as a standard product.

A sixth aspect of the present invention is to provide a method for evaluating a fixing member used to fix a toner, and the fixing member is produced by sequentially coating an elastic, layer and a separation layer onto a base element. In the method, the universal hardness test is carried out for each of first and second indentation depths from the surface side of the separation layer, and when the universal hardness for each of the first and the second indentation depths is in a predetermined value, the fixing member is regarded as a standard product.

A seventh aspect of the present invention is a method for evaluating a fixing member when the fixing member has a structure arrangement of a triple layer structure made of a base element, an elastic layer and a separation layer. In other words, the seventh aspect of the present invention is to evaluate the fixing member used to fix the toner, the fixing member being produced by sequentially coating the elastic layer and the separation layer onto the base element, in such a manner that the universal hardness test is carried out for each of indentation depths of 1 μm to 4 μm from the surface side of the separation layer, when the universal hardness HU for the indentation depth of 1 μm satisfies the relation, HU≦30 [N/mm²], and at the same time, when the universal hardness HU for the indentation depth satisfies the relation, HU≦12 [N/mm²], the fixing member is regarded as a standard product.

In the seventh aspect of the present invention, the above-mentioned universal hardness test is carried out at a test environment temperature of 25° C.

The universal hardness test can also be carried out at a test environment temperature of 200° C. Consequently, a eighth aspect of the present invention is to evaluate the fixing member used to fix the toner, the fixing member being produced by sequentially coating the elastic layer and the separation layer onto the base element, in such a manner that the universal hardness test is carried out at the test environment temperature of 200° C. for each of indentation depths of 1 μm to 4 μm from the surface side of the separation layer, when the universal hardness HU for the indentation depth 1 μm satisfies the relation HU≦10 [N/mm²], and at the same time, when the universal hardness HU for the indentation depth 4 μm satisfies the relation HU≦4 [N/mm²], the fixing member is regarded as a standard product.

In the seventh and the eighth aspects of the above-mentioned separation layer, it is preferable that a contact angle when a water-drop is contacted onto the surface of the layer is more than 95 degrees.

In the seventh and the eighth aspects of the present invention, the elastic layer is made of silicone gum.

In the seventh and the eighth aspects of the present invention, the separation layer is made of a material including at least one of polytetrafluoroethylene (PTFE) resin, polytetrafluoroethylene-perfluoro-alkoxyl (PFA) vinyl ether copolymer resin, and polytetrafluoroethylene-fluorinated ethylene propylene (FEP) copolymer resin.

In the seventh aspect of the present invention, the fixing member is a fixing belt or a thermal fixing roller.

Following is about the fixing belt of a ninth aspect to a thirteenth aspect of the present invention, and the twelfth aspect and the thirteenth aspect of the present invention are about the fixing belt of the triple layer structure made of the base element, the elastic layer, and the separation layer.

In the ninth aspect of the present invention, the fixing belt used to fix the toner, when a measurement is carried out at a test environment temperature of 25° C., the universal hardness HU for an indentation depth of 1 μm from the surface side of the belt satisfies the relation, HU≦30 [N/mm$^2$], and at the same time, when a universal hardness HU for an indentation depth of 4 μm from the surface side of the belt satisfies the relation, HU≦12 [N/mm$^2$].

In the tenth aspect of the present invention, the fixing belt used to fix the toner, when a measurement is carried out at a test environment temperature of 200° C., the universal hardness HU for an indention depth of 1 μm from the surface side of the belt satisfies the relation HU≦10 [N/mm$^2$], and at the same time, when a universal hardness for an indentation depth of 4 μm from the surface side of the belt satisfies the relation HU≦4 [N/mm$^2$].

In the ninth aspect and the tenth aspect of the fixing belt, it is preferable that a contact angle when a water-drop is contacted onto the surface of the belt is more than 95 degrees.

In the eleventh aspect of the present invention, the fixing belt used to fix the toner, the universal hardness test is carried out respectively at a room temperature and a running temperature of the belt for each of indentation depths of 1 μm to 4 μm from the surface side of the belt, when each of the universal hardness is compared at the same depth from the surface of the belt, the universal hardness at the room temperature is three times of the universal hardness at the running temperature.

In the twelfth aspect of the present invention, the fixing belt being produced by sequentially coating the elastic layer and the separation layer onto the base element, when a measurement is carried out at a test environment temperature of 25° C., the universal hardness HU for an indentation depth of 1 μm from the surface side of the separation layer satisfies the relation, HU≦30 [N/mm$^2$], and at the same time, when the universal hardens HU for an indention depth of 4 μm from the surface side of the separation layer satisfies the relation, HU≦12 [N/mm$^2$].

In the thirteenth aspect of the present invention, the fixing belt being produced by sequentially coating the elastic layer and the separation layer onto the base element, when a measurement is carried out at a test environment temperature of 200° C., the universal hardness HU for an indentation depth of 1 μm from the surface side of the separation layer satisfies the relation, HU≦10 [N/mm$^2$], and at the same time, when the universal hardness HU for an indention depth of 4 μm from the surface side of the separation layer satisfies the relation, HU≦4 [N/mm$^2$].

In the twelfth aspect and the thirteenth aspect of the separation layer, it is preferable that a contact angle when a water-drop is contacted onto the surface of the layer is more than 95 degrees.

In the twelfth aspect and the thirteenth aspect of the present invention, the elastic layer is made of silicone gum.

In the twelfth aspect and the thirteenth aspect of the present invention, the separation layer is made of a material including at least one of polytetrafluoroethylene (PTFE) resin, polytetrafluoroethylene-perfluoro-alkoxyl (PFA) vinyl ether copolymer resin, and polytetrafluoroethylene-fluorinated ethylene propylene (FEP) copolymer resin.

Following is about a thermal fixing roller of a fourteenth aspect to a sixteenth aspect of the present invention, and a seventeenth aspect and a eighteenth aspect of the present invention are about a thermal fixing roller of the triple layer structure made of the base element, the elastic layer, and the separation layer.

In the fourteenth aspect of the present invention, the thermal fixing roller used to fix the toner, when a measurement is carried out at a test environment temperature of 25° C., the universal hardness HU for an indention depth of 1 μm from the surface of the roller satisfies the relation, HU≦30 [N/mm$^2$], and the universal hardness HU for an indention depth of 4 μm from the surface of the roller satisfies the relation, HU≦12 [N/mm$^2$].

In the fifteenth aspect of the present invention, the thermal fixing roller used to fix the toner, when a measurement is carried out at a test environment temperature of 200° C., the universal hardness HU for an indention depth of 1 μm from the surface of the roller satisfies the relation, HU≦10 [N/mm$^2$], and the universal hardness HU for an indention depth of 4 μm from the surface of the roller satisfies the relation, HU≦4 [N/mm$^2$].

In the fourteenth aspect and the fifteenth aspect of the thermal fixing roller, it is preferable that a contact angle when a water-drop is contacted onto the surface of the roller is more than 95 degrees.

In the sixteenth aspect of the present invention, the thermal fixing roller used to fix the toner, the universal hardness test is respectively carried out at a room temperature and a running temperature of the roller for each of indention depths of 1 μm to 4 μm from the surface of the roller, when each of the universal hardness is compared at the same depth from the surface of the roller, the universal hardness at the room temperature is three times of the universal hardness at the running temperature.

In the seventeenth aspect of the present invention, the thermal fixing roller being produced, by sequentially coating the elastic layer and the separation layer onto the base element, when a measurement is carried out at a test environment temperature of 25° C., the universal hardness HU at an indention depth of 1 μm from the surface side of the separation layer satisfies the relation, HU≦30 [N/mm$^2$], and the universal hardness HU at an indention depth of 4 μm from the surface side of the separation layer satisfies the relation, HU≦12 [N/mm$^2$].

In the eighteenth feature of the present invention, the thermal fixing roller being produced by sequentially coating the elastic layer and the separation layer onto the base element, when a measurement is carried out at a test environment temperature of 200° C., the universal hardness HU at an indentation depth of 1 μm from the surface side of the separation layer satisfies the relation, HU≦10 [N/mm$^2$] and the universal hardness HU at an indention depth of 4 μm from the surface side of the separation layer satisfies the relation, HU≦4 [N/mm$^2$].

In the seventeenth aspect and the eighteenth aspect of the separation layer, it is preferable that a contact angle when a water-drop is contacted onto the surface of the layer is more than 95 degrees.

In the seventeenth aspect and the eighteenth aspect of the present invention, the elastic layer is made of silicone gum.

In the seventeenth aspect and the eighteenth aspect of the present invention, the separation layer is made of a material including at least one of polytetrafluoroethylene (PTFE) resin, polytetrafluoroethylene-perfluoro-alkoxyl (PFA) vinyl ether copolymer resin, and polytetrafluoroethylene-fluorinated ethylene propylene (FEP) copolymer resin.

A nineteenth aspect of the present invention is about a thermal fixing apparatus. In other words, the nineteenth aspect of the present invention includes a heat roller) which is heated by a heating source, a fixing roller, which is disposed parallel to the heat roller, a fixing belt, which is wound between the fixing roller and the heat roller, and is heated by the heat roller as well as is rotated by the both rollers, and a press roller, which is contacted onto the surface of the fixing belt and forms a nip section between said Sing belt. In the aspect, when the universal hardness test is carried out for an indentation depth of 1 μm from the surface of the fixing belt at a room temperature, the universal hardness HU of the fixing belt satisfies the relation, $HU \leq 30$ [N/mm$^2$].

A twenty aspect of the present invention is about an image forming apparatus which includes the thermal fixing apparatus described in the nineteenth aspect of the present invention. In the twenty aspect, when the universal hardness test is carried out for an indentation depth of 1 μm from the surface side of the fixing belt at a room temperature, the universal hardness HU of the fixing belt satisfies the relation, $HU \leq 30$ [N/mm$^2$].

BRIEF DESCRIPTION OF THE DRAWINGS

FIG. 11 is a diagram showing a relationship between the universal hardness and the test environment temperature at varied indentation depths, where the universal hardness is determined by averaging the data in FIG. 8.

FIG. 12 is a diagram showing a relationship between the universal hardness and the indentation depth.

DESCRIPTION OF THE PREFERRED EMBODIMENTS

Referring now to the accompanying drawings, several embodiments of the present invention will be described below.

Figure 1A:
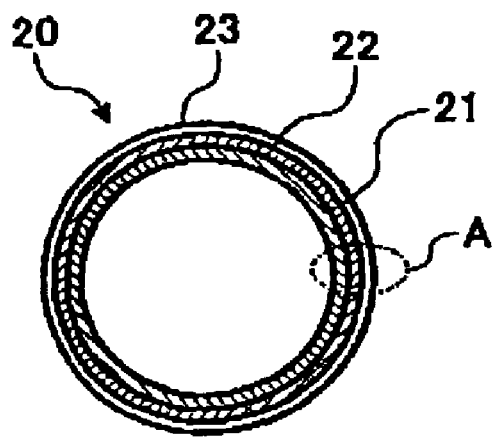
FIG. 1A is a sectional view of a fixing belt according to the present invention.
Figure 1B:
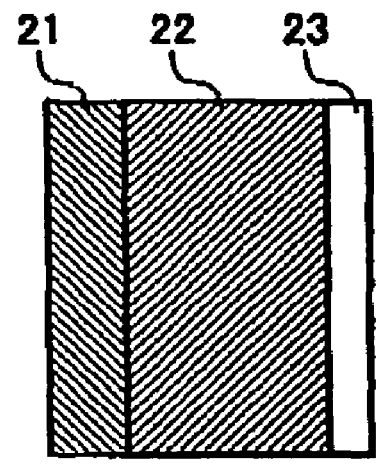
FIG. 1B is an enlarged sectional view of an area A in FIG. 1A.

FIG. 1 shows a fixing belt 20 according to the present invention. FIG. 1A is a sectional view of the fixing belt 20. FIG. 1B is an enlarged sectional view of an area A in FIG. 1A. As shown in FIG. 1, the fixing belt 20 includes a base element of a belt 21, an elastic layer 22, and a separation layer 23. These are built up sequentially from the base element 21, the elastic layer 22, and the separation layer 23.

The base element 21 is made of a heat resistant material. Such a heat resistant material is a metal material, such as stainless still SUS, nickel or the like, or a heat resistant resin, such as polyimide, polyamideimide, fluorocarbon resin or the like. In the case of such a metal material, it is preferable that the layer thickness of the base element 21 should be less than 100 μm, taking the bending of the belt into account. In the case of such a heat resistance resin, it is preferable that the layer thickness of the base element 21 should be 30 to 200 μm from the viewpoint of a heat capacity (a smaller thickness is more advantageous due to the reduction in the standby time) and the mechanical strength (a greater thickness is more advantageous thereto). In this case, the heat capacity is small tag the reduction in the standby time into account, in other words, the thinner layer thickness of the base element 21 is advantageous. Moreover, it is advantageous that the layer thickness of the base element 21 is thicker taking the strength of the belt into account. However, at this point, the layer thickness of the base element 21 is determined 30 μm to 200 μm from a comprehensive judgment.

The elastic layer 22 is used to obtain the evenness and uniformity in a glossy image, and a flexible surface of the belt may be obtained by coating this elastic layer 22. In order to ensure the heat resistance at a relatively high temperature (less than 200° C.), in the case of fixing, a silicone gum is used as a material of the elastic layer 22, and its thickness should be preferably 200 μm or so.

The material for the separation layer 23 may be selected from fluorocarbon resin such as polytetrafluoroethylene (PTFE) resin, polytetrafluoroethylene-perfluoro-alkoxyl (PFA) vinyl ether copolymer resin, polytetrafluoroethylene-fluorinated ethylene propylene (FEP) copolymer resin or the like, or a mixture of these resins, or a heat resistant resin in which such a fluorocarbon resins is dispersed. The thickness of the separation layer 23 should be preferably 200 μm or so.

The covering of the elastic layer 22 with the separation layer 23 provides a good toner separation ability and also prevents powder from adhering to a recording paper even if silicone oil or the like is not used (the oil-less approach). Generally, the above-mentioned resin having a good toner separation ability has no such an elasticity as in gum material, so that there is a danger that unevenness appears on the gloss surface of the recording paper, when the separation layer 23 having a relatively large thickness is coated on the elastic layer 22. In to other words, the separation layer 23 has to be coated on the elastic layer 22 without any reduction in the flexibility thereof in order to consistently ensure both the suppression of the unevenness in the glossy surface of the recording paper and the separation ability of the toner and/or the paper powder. Accordingly, it is preferable that the material for the separation layer 23 should be as flexible as possible and that the thickness thereof should be as thin as possible.

As described above, the requirements as for the fixing belt having three layers of the base element 21, the elastic layer 22 and the separation layer 23 resides in the rationalization of the surface state and the numerical characterization of the belt. The surface of the belt comes into contact with an unfixed toner image and serves transferring a heat to the toner therein, so that the fig of the toner image onto the recording paper is carried out by pressing the belt onto the paper. When, however, the surface of the belt is uneven, the state of contact is different from the top area to the bottom area of the belts. Of course, such a difference in the contact provides a marked difference in the heat transfer and in the pressure applied to the toner, thereby causing unevenness to being generated in the glossy surface of the recording paper. The elastic layer 22 serves reducing or moderating the difference in the contact state at the top area and bottom areas with the aid of its elasticity.

Figure 2:
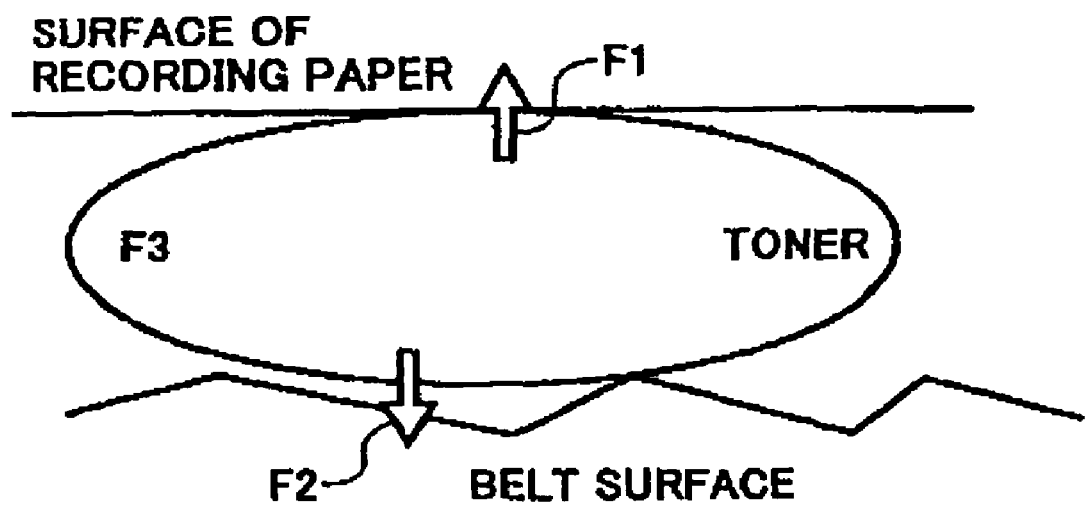
FIG. 2 is a schematic sectional view of a thermal fixing for explaining the mechanism in which toner is fixed on a recording paper.

Referring to FIG. 2, the influence of the surface state of the belt on the uniformity in an image as well as the fixing characteristic will subsequently be described. In FIG. 2, symbols F1, F2 and F3 mean an adhesive force between the recording paper and the toner, an adhesive force between the belt and the toner and a cohesive force of the toner, respectively.

Firstly, regarding the uniformity in the image, it is assumed that the unevenness in the glossy surface (image) results from the difference in the state of contact between the toner and the convex or concave areas (the top or bottom areas) of the surface of the belt. When the fixing roller and the press roller are pressed against each other, the top area is flattened due to the elasticity of the belt surface. In this case, the degree of flatness depends on the magnitude of the elasticity as well as the shape of the belt surface. When the material is the same in varied areas on the belt surface, it depends on only the shape of the belt surface. A decrease in the number of top areas having a smaller height causes the deviation in the contact state to be reduced due to the unevenness. In conjunction with this, unevenness in the glossy surface (image) (i.e. unevenness in the brilliance) can be seen as a matt surface, so that it is referred to as a matt pattern or surface.

Secondly, the fixing characteristic (the separation ability) will be explained. The fixing characteristic used herein means the separation ability (the fixing temperature difference=the hot offset temperature−the cold offset temperature). In other words, the fixing characteristic indicates how the fixing temperature difference is changed by the state of the belt surface. Generally, the cold offset implies the state in which the toner is not sufficiently fixed on the recording paper. These results from the incomplete fusion of the toner (due to a smaller fixing temperature) and the incomplete press force between the belt and the recording paper.

The surface roughness is one of factors for evaluating the state of the belt surface. As a characteristic value, the mean roughness Ra determined by averaging the roughness along the center line, the mean roughness Rz determined by averaging the roughness over ten points or the like is generally used. When either Ra or Rz becomes large, both the magnitude of heat transfer to the toner and the press force decrease at the bottom areas, thereby causing the cold offset to be induced with an increasing probability.

The hot offset is a phenomenon in which molten toner is adhered to the belt surface and remains thereon. The phenomenon takes place when the adhesion force F2 between the belt and the toner is greater than the cohesive force F3 of the toner. When the material is the same in the varied areas of the belt surface, an increase in the area of the contact surface with the toner provides an increase in the adhesion force F2 between the belt and the toner.

In the following, a method for numerically characterizing the surface hardness according to the present invention will be described.

As for the surface hardness regarded as another important factor for evaluating the surface property, it is difficult to find the correlation between the surface hardness and the important image property in the full color fixing apparatus, i.e., the latter being the evenness in the glossy surface (image) and the image transparency of an OHP sheet, as described in the survey of the prior art, and therefore it is difficult to obtain a reproducible image quality.

In view of these facts, the present inventors investigated the correlation between the hardness of the belt surface and the image quality by utilizing the universal hardness HU defined in the German Industrial Standard DIN50359-1. The results of the investigation revealed a marked correlation between "the amount of HU for a specified indentation depth from the surface" and "the evenness in the gloss surface (image) (matt pattern)".

The universal hardness HU used herein will be described:

Traditionally, the surface hardness in a micro surface area has been determined with a micro Vickers hardness test method or the like, in which an indentation probe is pressed onto the surface of a material to be tested and then the indentation depth of the indentation probe from the surface is measured under an optical microscope after the load is released. On the contrary, in the method for measuring the universal hardness HU, the hardness is determined by directly reading the indentation depth in the sate of applying a weight to the indentation probe. In this case, the indentation depth is measured for the weight having not only one value but also varied values by stepwise increasing the weight, so that varied indentation depths are deterred for the individual test weights. This method makes it possible to determine the hardness for a micro surface area of an elastic body, on the surface of which the trace of the indentation can hardly be retained and to determine the hardness of a heterogeneous surface layer.

However, the following two points have to be taken into account in the actual measurement:

The thickness of a test piece should be more than ten times greater than the indentation depth.

The indentation depth should be more than twenty times greater than the surface roughness Ra of a surface of the test piece, when the measurement is carried out with an uncertainty of less than 10%.

The surface roughness Ra of a usual fixing member is 0.1 μm-0.2 μm. In this case, therefore, the indentation depth have to be set greater than 2-4 μm. However, it is possible to reduce the minimum value of the indentation depth by applying a smoothed treatment such as polishing or the like, on the surface of the fixing member.

The universal hardness HU can be obtained from the following equation:

$$HU = F/S$$
$$= F/26.43h^2 [N/mm^2]$$

where

F: test load [N]

S: the surface area of the indentation probe under the test load [mm$^2$] and h: the indentation depth under the test load [mm]

and the indentation probe is a quadrangular pyramid-shaped diamond indentation probe (Vickers indentation probe) having an angle of 136° between the facing surfaces.

In the present embodiment, with respect to the fixing belt 20, the universal hardness test is carried out for each of indentation depth 1 μm to 4 μm from the surface side of the separation layer 23 at the test environment temperature of 25° C., and the fixing belt 20 can be regarded as a standard or utility product, when the following two conditions are satisfied: The universal hardness HU at the indentation depth of 1 μm is HU≦30 [N/mm$^2$] and the universal hardness HU at the indentation depth of 4 μm in is HU≦12 [N/mm$^2$].

In the present embodiment, moreover, with respect to the fixing belt 20, the universal hardness test is carried out for each of indentation depths 1 μm to 4 μm from the surface side of the separation layer 23 at a test environment temperature of 200° C., and the fixing belt 20 can be regarded as a standard or an utility product, when the following two conditions are satisfied: The universal hardness HU at the indentation depth of 1 μm is HU≦10 [N/mm$^2$] and the universal hardness HU at the indentation depth of 4 μm is HU≦4 [N/mm$^2$].

At this point, the test environment temperature 25° C. is suited to a room temperature, and the test environment temperature 200° C. is suited to a running temperature in which the fixing belt is exposed at the time of fixing a toner. The upper limit of the universal hardness HU at the indentation depth of 1 μm from the surface of the separation layer 23 is respectively set to 30 [N/mm$^2$] when the test environment temperature is 25° C. and 10 [N/mm$^2$] when the test environment temperature is 200° C. The universal hardness HU under the room temperature is three times of the universal hardness under the running temperature. The upper limit of the universal hardness HU at the indentation depth of 4 μm from the surface of the separation layer 23 is respectively set to 12 [N/mm$^2$] when the test environment temperature is 25° C. and 4 [N/mm$^2$] when the test environment temperature is 200° C. The universal hardness HU under the room temperature is also three times of the universal hardness under the running temperature.

The universal hardness test for each independent depth 1 μm to 4 μm from the surface of the separation layer 23 is carried out respectively under the room temperature and the running temperature of the fixing belt 20. The respective universal hardness HU at the same depth from the surface of the separation layer 23 is compared. If the universal hardness HU under the room temperature is three times of the universal hardness HU under the running temperature, the fixing belt 20 can be regarded as a standard product or a utility product.

In the present embodiment, the evaluation of the hardness for the fixing belt is exclusively described. However, the present invention can also be applied to a thermal fixing roller, in which an elastic layer and A separation layer are laminated on a core body, i.e., a base element.

Embodiment

In conjunction with the above, an investigation regarding the influence of the universal hardness on the image quality was carried out.

An unfixed image was formed on a recording paper and then fixed on the recording paper under the following conditions, using a thermal fixing apparatus. In this case, using fixing belts whose surface having different values in the universal hardness, the relationship between the universal hardness and the matt image (the unevenness in the glossy surface) after fixing was investigated.

Image to be evaluated (unfixed image)

Toner: magenta color

Amount of deposition: 0.8-0.9 mg/cm$^2$, and

Type of paper: T 6200 (62 kg paper)

In the following, a full color thermal fixing apparatus including the fixing belt according to the present embodiment will be described. A fixing belt 20 is used in the thermal fixing apparatus as shown in FIG. 3. The fixing belt 20 is wound in an appropriate tension between a heating roller 31 and a fixing roller 32 (the mechanism for applying the tension is not shown). Moreover, a press roller 38 is disposed in parallel to the filing roller 32, and further the fixing belt 20 wound around the fixing roller 32 is pressed against the side of the fixing roller 32 so as to come into contact therewith by the press roller 33 (the press contact mechanism is not shown).

Figure 3A:
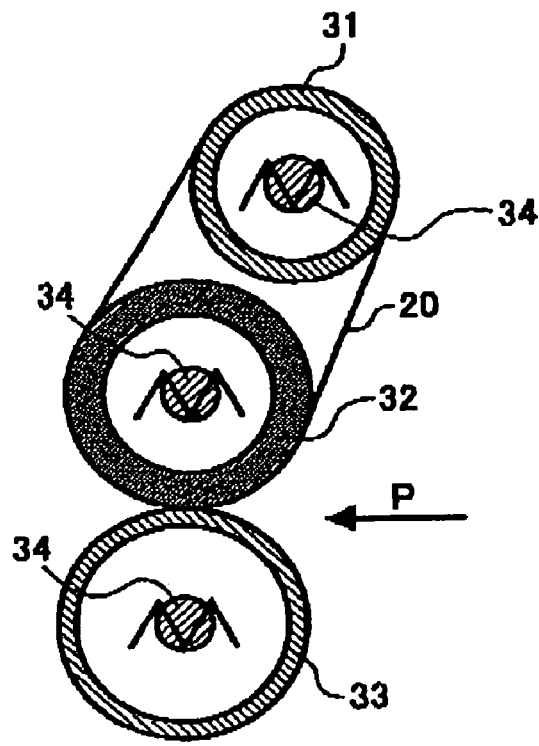
FIG. 3A is a schematic sectional view of a thermal fixing apparatus in an embodiment.
Figure 3B:
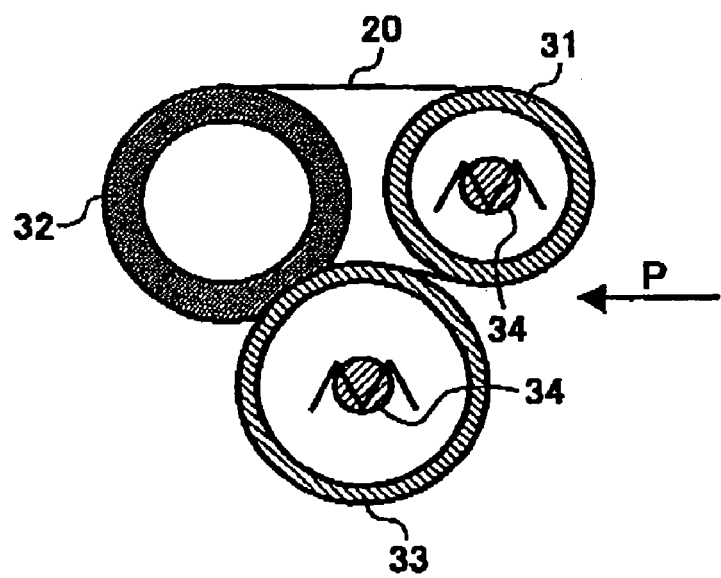
FIG. 3B is a schematic sectional view of a thermal firing apparatus in another embodiment.

Generally, there are two types of the press contact method for pressing the fixing belt 20 by the press roller 33, as shown in FIG. 3A and FIG. 3B. In the method of FIG. 3A (RICHO Co. Ltd: Imagio color (®) 3100 or the like), a nip section comprising only a press roller 33 and a fixing roller 32 (along with a fixing belt interposed therebetween) is employed. However, in the method of FIG. 3B (RICOH Co. Ltd: Ipsio color (®) 8000 or the like), not only a nip section comprising a press roller 33 and a fixing roller 32, but also another nip section, in which the fixing belt 20 puts between the press roller 33 and a heating roller 31, is employed. Such a difference in the structural arrangement practically provides a difference between the two methods as for the standby time, the transportation ability, the sheet-separation ability and others. Since, however, the properties of a fixing belt itself were exclusively studied in the present embodiment, the influence of the belt on the image quality was investigated only for the fixing method as shown in FIG. 3A.

In FIG. 3, halogen lamps 34 are mounted in the inside of the heating roller 31 to heat the same. The number and the power consumption of the halogen lamps 34 are adjusted in accordance with the specification (the standards) regarding the fixing temperature, the line speed, the standby time and the surface temperature variation on the belt surface. Generally, halogen lamps 34 are mounted in the inside of each of the heating roller 31, the fixing roller 32 and the press roller 33 in the arrangement of FIG. 3A, whereas the halogen lamps 34 are mounted in the inside of each of the heating roller 31 and the press roller 33 in the arrangement of FIG. 3B. In FIG. 3, arrows respectively indicate the direction of feeding the recording paper.

The following test conditions are employed:

Fixing test machine: Improved fixing unit in the Imagio color 3100,

Fixing roller: φ40 mm, silicone gum elastic layer 5 mm+FLC30 μm, gum hardness 62.5 Hs (Asker C), Press roller: φ40 mm, silicone gum elastic layer 2 mm+PFA tube 50 μm, gum hardness 72 Hs (asker C)

Nip pressure: 45 kgf on one side,

Line speed: 200 mm/s,

Universal hardness test machine: Fischer scope H-100

Test load: 0.4 mN-1000 mN (≈300 mN in this test)

Regarding to the evaluation of a matt image, the following ranks of evaluation are used (for the rank halfway between the ranks, 0.5 is added to the lower rank):

Rank 5: no significant unevenness in the matt image standard level.

Rank 4: between rank a and rank 5 standard level.

Rank 3: unevenness partially generated in matt image standard level.

Rank 2: between rank 1 and rank 3 impermissible level.

Rank 1: unevenness generated over the entire matt image impermissible level.

Figure 4:
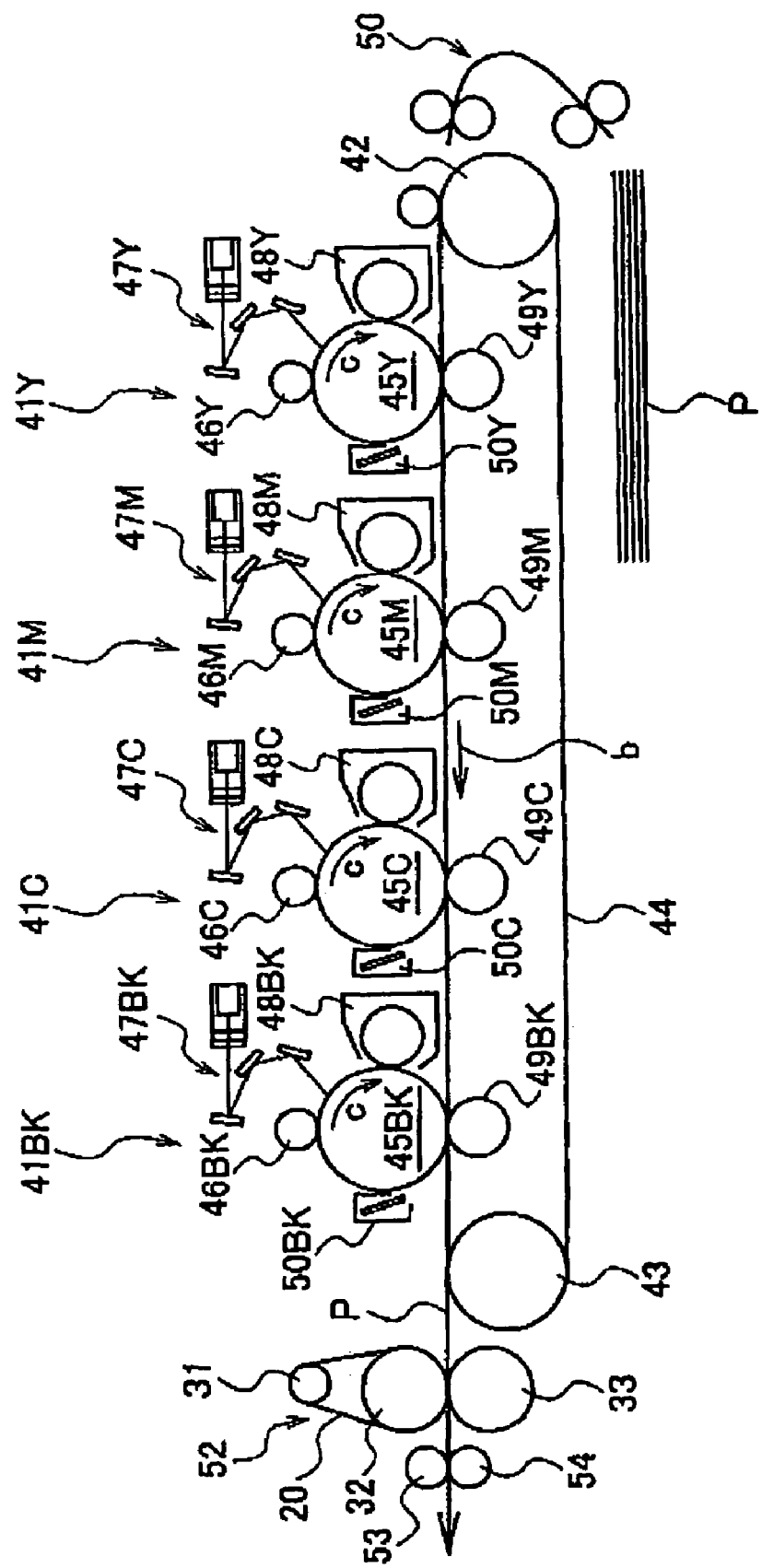
FIG. 4 is a schematic sectional view of an image forming apparatus in which the thermal fixing apparatus of FIG. 3A is equipped.

FIG. 4 shows the schematic structure of the image forming apparatus according to the present invention. The image forming apparatus shown in FIG. 4 is a full-color printer of a four series tandem system, and the thermal fixing apparatus shown in FIG. 3A is equipped.

This full-color printer equips four pairs of image forming sections such as 41Y, 41M, 41C, and 41Bk for respectively forming four colors of toner images such as yellow, magenta, cyan, and black.

Transport belt 44 which is wound between a pulley 43 and a pulley 44 is disposed in the lower portion of the image forming sections 41Y, 41M, 41C, and 41Bk. The transport belt 44 is moved to the direction arrow b by a driving device (not shown), and transports a recording paper P through the image forming sections 41Y, 41M, 41C, and 41Bk.

Each image forming section 41Y, 41M, 41C, and 41Bk has the same structural arrangement, so that the explanation is mentioned only for the image forming section 41Y herein. In the image forming sections 41M, 41C, and 41Bk for other colors, the detailed explanation will be skipped by applying the same number for the same portion with the image forming section 41Y.

The image forming section 41Y includes a photoconductor drum 45Y, which is rotatably contacted to the transport belt 44, in the near central position of the image forming section 41Y. The periphery area of the photoconductor drum 45Y is provided with a electrification device 46Y in which the surface of the photoconductor drum 45Y is charged predetermined electrical potential, an exposure device 47Y in which the charged surface of the drum is exposed based on a color-decomposed signal, and an electrostatic latent image is formed onto the surface of the drum, a development device 48Y in which the electrostatic latent image formed on the surface of the drum is developed by providing a yellow toner, a transfer roller 49Y, which transfers the developed toner image onto the recording paper P transported by the transport belt 44, a cleaner 50Y, which eliminates residual toner remained on the surface of the drum without being transported, and a discharge lamp (not shown), which eliminates the charge remained on the surface of the drum. These devices are sequentially arranged along with the rotating direction of the photoconductor drum 45Y.

One side (right side of the view) of the transport belt 44 is provided with a feeding mechanism 51 to feed the recording paper P on the transport belt 44. The other side (left side of the view) of the transport belt 44 is provided with a thermal fixing apparatus 52, and the recording paper P transported by the transfer belt 44 is continuously provided thereto.

As shown in FIG. 3A, the thermal fixing-apparatus 52 includes the heat roller 31 and the fixing roller disposed in the lower portion of the heat roller 32. The endless fixing belt 20 is wounded between the heat roller 31 and the fixing roller 32. A press roller 33 is disposed in the lower potion of the fixing roller 32, and the fixing belt 20 is contacted thereto by the pressure of the press roller 33. The halogen lamps 34 (FIG. 3A) are arranged inside the fixing roller 32 and the press roller 33 (not shown in FIG. 4).

The recording paper P provided from the transport belt 44 is heated and pressed by passing through between the fixing belt 20 and the press roller 33, and then the toner image on the recording paper P is fixed thereto. The recording paper P in which the toner image is fixed is discharged to the downstream side of the transport path through discharge rollers 53 and 54.

An image forming apparatus (a full-color printer), which equips the thermal fling apparatus shown in FIG. 3B will be described as follows. Such an image forming apparatus includes the image forming sections 41Y, 41M, 41C, 41Bk, the transport belt 44, and the feeding mechanism 51 as shown in FIG. 4.

Figure 5:
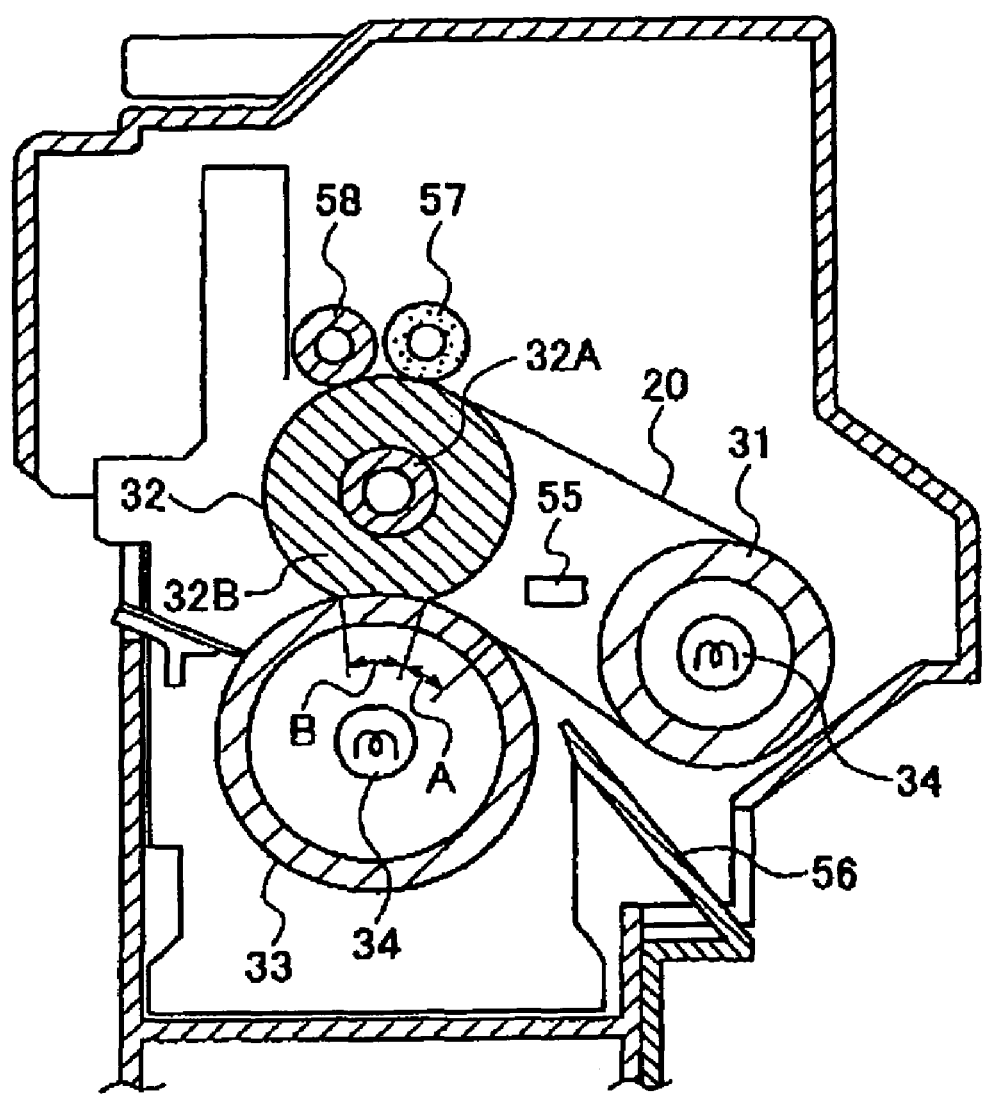
FIG. 5 is a longitudinal sectional view of an image forming apparatus in which the thermal fixing apparatus of FIG. 3B is equipped.

As shown in FIG. 5, the image forming apparatus is provided with a heat roller 31 and a fixing roller 32, which is disposed in a downward oblique direction of the heat roller 31. An endless fixing belt 20 is wounded between the heat roller 31 and the fixing roller 32. The press roller 33 is disposed in under the fixing roller 32, and the fixing belt 20 is contacted to the fixing roller 32 by the pressure of the press roller 33. Halogen lamps are arranged inside the heat roller 31 and the press roller 33. The heat roller 31 is energized to the direction away from the fixing roller 32 by means for energizing such as a spring (not shown) so that an appropriate predefined tension is provided for the fixing belt 20.

The fixing roller 32 includes a core 32A, an elastic layer 32B of a heat resistance porous layer, which covers this core 32A. The fixing roller 32 is energized in the direction, which contacts to the press roller 33 with the pressure of the fixing roller 32, by means for energizing such as a spring (not shown).

The fixing roller 32 is contacted to the press roller 33 in such a manner that an angle, which is formed by a line connecting a shaft center of the fixing roller 32 and a shaft center of the heat roller 32 adopted the shaft center of the fixing belt 32 as a vertex and a line connecting a shaft center of the heat roller 33 and a shaft center of the press roller 33 becomes a shape angle. Consequently, a first fixing portion A contacting to the fixing belt 20 in the area in which the press roller 33 does not face to the fixing roller 32 and a second fixing portion B contacting to the fixing belt 32 through the fixing belt 20 are formed. These fixing portions A and B are adapted to put and sandwich and heat the recording paper.

A thermistor 55 is disposed facing to both the heat roller 31 and the press roller 33, and the temperatures of the heat roller 31 and the press roller 33 are thereby detected.

In the view, reference numeral 56 denotes a guide for guiding a fixable recording paper toward a first fixing portion A, reference numeral 57 a coating roller of oil for preventing an offset, and reference numeral 58 a cleaning roller.

First Embodiment

Generally, it is know that a matt image becomes prominent in a highly glossy image Using a kind of toner (toner No. 1) providing a glossiness of 5-8% (magenta color: 0.8-0.9 mg/cm$^2$) at a fixing temperature of 160-170° C. as well as another kind of toner (toner No. 2) providing a glossiness of 10-15% (magenta color: 0.8-0.9 mg/cm$^2$) at the same fixing temperature under the above-mentioned conditions, the relationship between the universal hardness and the glossiness of the image was studied for varied degree of gloss in the image.

Figure 6:
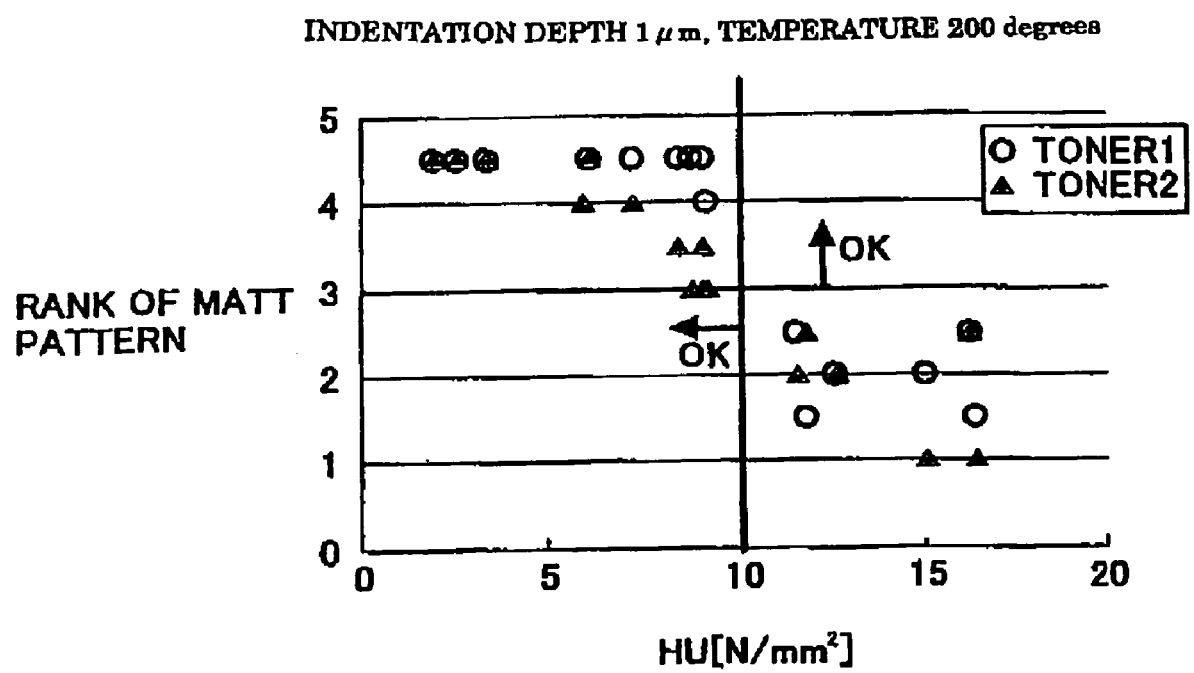
FIG. 6 is a diagram showing a relationship between the universal hardness and the rank of matt pattern.
Figure 7:
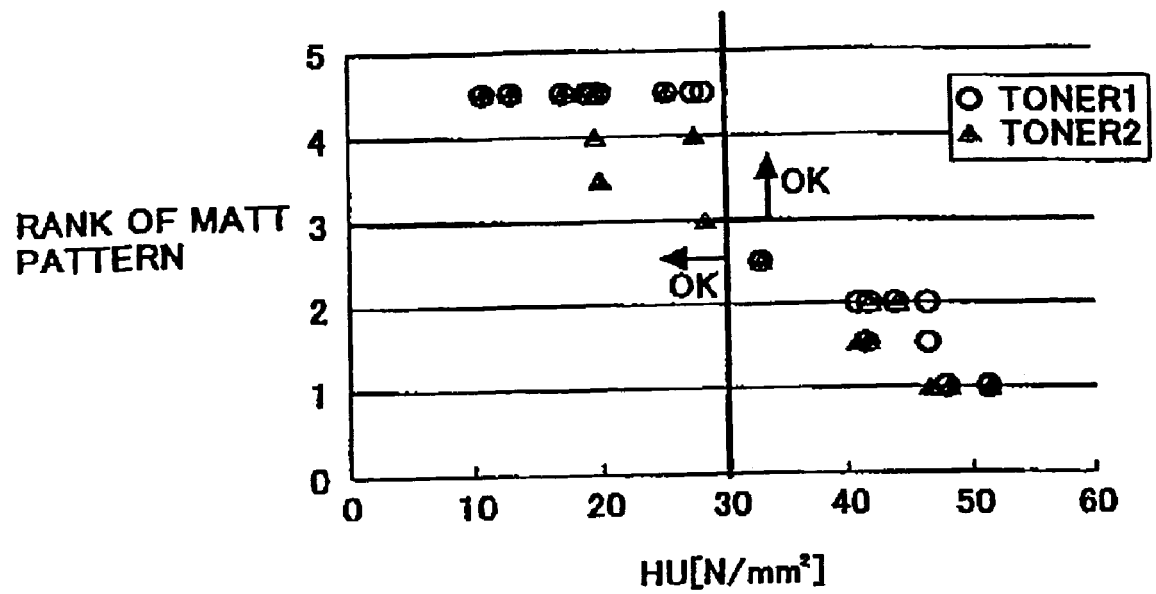
FIG. 7 is a diagram showing a relationship between the universal hardness and the rank of matt pattern.
Figure 8:
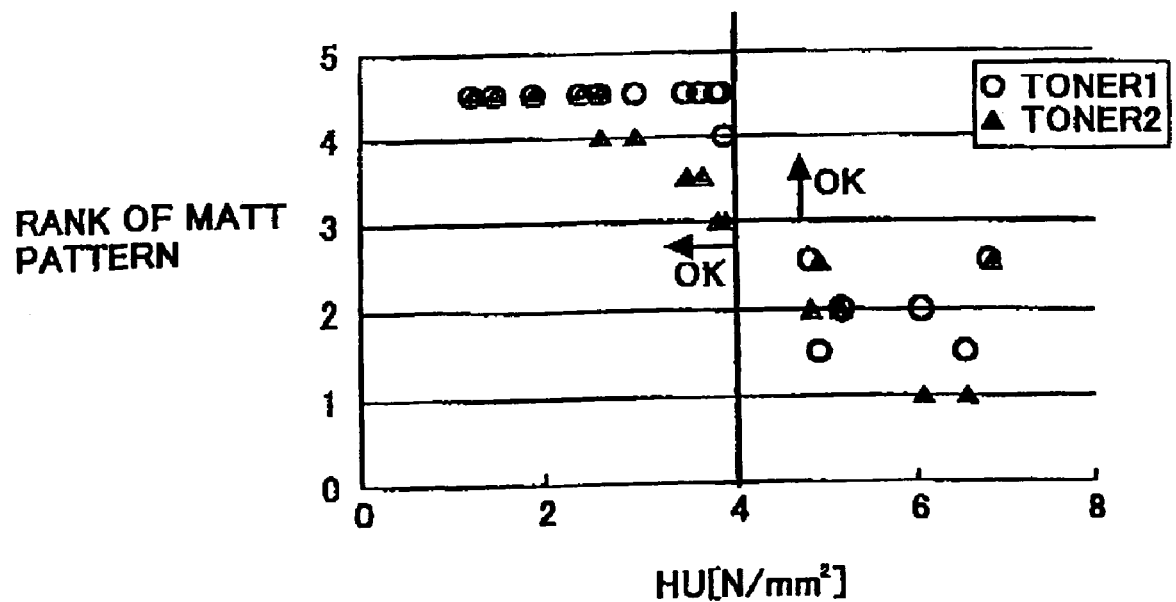
FIG. 8 is a diagram showing a relationship between the universal hardness and a rank of matt pattern.
Figure 9:
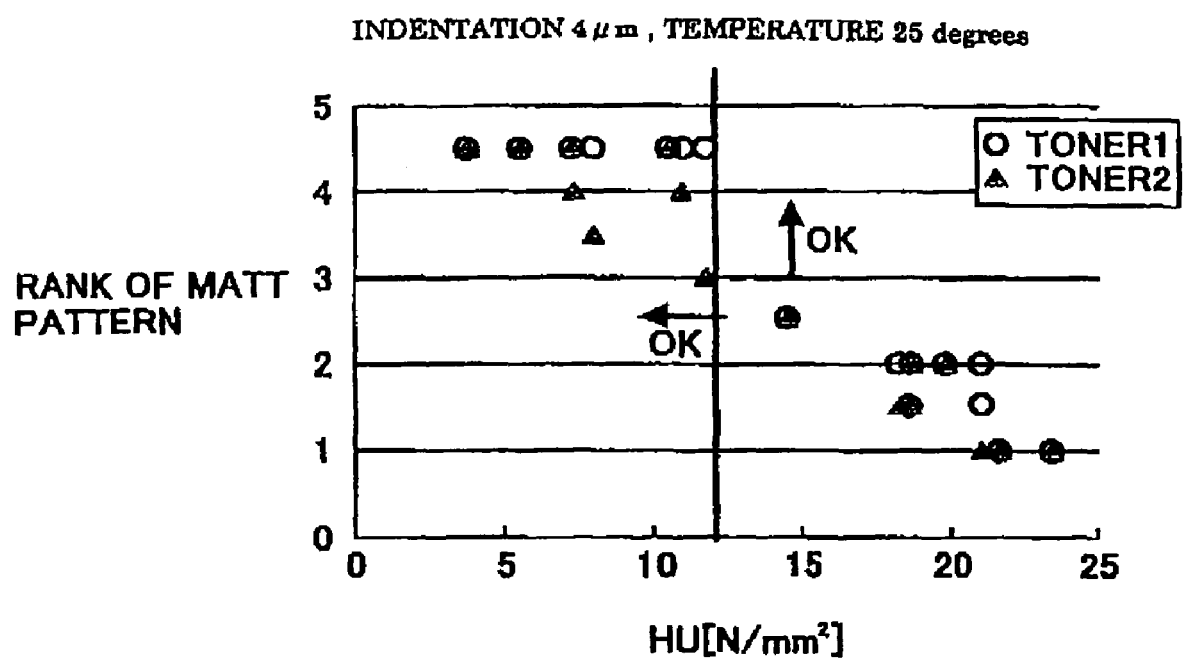
FIG. 9 is a diagram showing a relationship between the universal hardness and the rank of matt pattern.

FIGS. 6 to 9 show the obtained results of the relationship between the universal hardness and the rank of the matt pattern, in which case, FIG. 6 shows the data for an indentation depth of 1 μm at a test environment temperature of 200° C.; FIG. 7 shows the data for an indentation depth of 1 μm at a test environment temperature of 25° C.; FIG. 8 shows the data for an indentation depth of 4 μm at a test environment of 200° C.; and FIG. 9 shows the data for an indentation depth of 4 μm at a test environment temperature of 25° C. From the data, it can be recognized that an excellent uniformity in the gloss (rank of more than 3) can be obtained, when the universal hardness HU satisfies a range shown in following equations (1) and (2) or equations (3) and (4).

$$HU1 \leq 30 [N/mm^2] \quad (1)$$

and $$HU2 \leq 12 [N/mm^2] \quad (2)$$

where HU1 and HU2 are magnitudes of universal hardness for the indentation depths of 1 to 4 μm from the surface of the separation layer at the test environment temperature of 25° C., respectively.

$$HU3 \leq 10 [N/mm^2] \quad (3)$$

and $$HU4 \leq 4 [N/mm^2] \quad (4)$$

where HU3 and HU 4 are magnitudes of universal hardness for the indentation depths of 1 to 4 μm from the surface of the separation layer at the test environment temperature of 200° C., respectively.

From the results for equations (1) to (4), the universal hardness can be estimated for an arbitrary indentation depth within a range of 1 μm-4 μm at a test environment temperature of 25° C. or 200° C. Similarly, the universal hardness can be estimated at an arbitrary test environment temperature (except for the temperature greater than the resin decomposing temperature), when the indentation depth is set 1 μm or 4 μm.

In the following, the reason why 1 μm or 4 μm should be selected as the indentation depth will be described. As described in the survey of the prior art, no explicit numerical characterization has been given for the hardness of the belt (elements) and the evenness in the gloss. In particular, it is not clear whether the evenness in the gloss results form the flexibility of the entire belt including the bending of the base element or the flexibility of the outermost surface, i.e., extremely restricted depth area of the fixing belt. In the measurement of the hardness of the outermost surface, the indentation depth should be set less than 1 μm, because there is a minimum thickness of 10 μm or so in the separation layer and also there is the above-described restriction on the layer thickness in the measurement. If the belt can be regarded as a laminated structure (base element+elastic layer+separation layer), the measurement can be carried out for a grater indentation depth. When, for example, the base element having a 50 μm thickness, the elastic layer having a 200 μm thickness and the separation layer having a 30 μm thickness are employed, the total layer thickness becomes 280 μm and, therefore, the measurement can be carried out for an indentation depth of not more than 28 μm. The present inventors experimentally confirmed a marked relationship between the universal hardness and the evenness in the gloss for an indentation depth of 1-20 μm.

Regarding the indentation depth, there is no special meaning for adopting either 1 μm or 4 μm. For instance, an indentation depth of 2 μm or 3 μm interposing between these values can also be adopted, and a similar correlation between the universal hardness and the evenness in the gloss can be obtained. In this case, the relationship between the hardness and the evenness in the gloss can be obtained within the rage shown in the present embodiment, if the measurement is carried out for the belt (elements) at each of indentation depths of 1 μm and 4 μm.

Furthermore, the reason why 25° C. or 200° C. should be employed as the test environment temperature will be described. In accordance with the German Industry Standard DIN 50359-1, the specified measurement temperature is 10-35° C. In view of this fact, the measurement temperature of 25° C. was adapted in the present embodiment. The Fischer scope H-100 used in the present embodiment was capable of varying the measurement temperature, so that the measurement was carried out at an environment temperature of 200° C. near the fixing temperature, and the relationship between the hardness and the evenness in the gloss was investigated.

From the results in FIGS. 6 to 9, it can be recognized that the toner No. 1 has a greater magnitude of allowance for the matt image than the toner No. 2. In other words, an increased glossiness in an image provides an increased unevenness in the gloss (matt pattern). This means that, in order to obtain a high glossy image, the toner should be fixed onto a recording paper after sufficiently fusing the toner to reduce the viscosity thereof, and the toner having such low viscosity should be pressed onto the surface of an element having a greater magnitude of flexibility.

In the following, the influence of the structural arrangement of the fixing belt on the universal hardness was investigated. In this case, the universal hardness, the durability and the toner separation ability were studied for fixing belts having various kinds of material in varied thickness of the elastic layer and the separation layer (embodiments 1-5 and comparative examples 1-7) as shown in Table 1. The results are also shown in Table 1.

Table 1

The structural arrangement of the belts is as follows:

Base element: Polyimide resin; ϕ60 mm; the surface length, 331 mm; layer thickness, 90 μm.

Elastic layer: Silicone gum; hardness, 25° C. (JIS K 6301); layer thickness; Three level (non, 200 μm)

Separation layer: material of three level; PFA No. 1 (a reduced flexibility), PFA No. 2 (an increased flexibility), FEP; layer thickness, 10-40 μm.

In the following, the method for producing the fixing belt will be described. A blade coating method was employed to form the elastic layer (after diluting the resin with a solvent, a spray coating method, a dipping coating method or the like can be employed). In the present embodiment, the silicone gum was used as a material for the elastic layer, and it is known that the silicone gum has an excellent heat resistance, because its upper usable temperature in the continuous operation is 200° C. As described above, fluorosilicone gum, fluorocarbon gum or the like can also be used as a gummy (elastomer) material used for the elastic layer. At present, however, only the fluorosilicone gum is usable in various coating processes, such as the spray coating, the dipping coating, blade coating, molding or the like. In conjunction with this, the fluorosilicone gum is most preferable with respect to the cost. As a result, it was found that the silicone gum is currently most preferable as a material for the elastic layer, when a layer having a thickness of 200 μm or so is coated with a small thickness scattering as well as with a greater surface smoothness.

The spray coating method was employed to form the separation layer. Moreover, it is noted that, a primer can be sandwiched or interposed between the polyimide base element and the elastic layer as well as between the elastic layer and the separation layer, as the necessity arises, and then the primer provides no significant effect on the properties of the fixing belt.

From the results in Table 1, it is found that the values of the universal hardness required for obtaining the above-mentioned evenness in the glossy image are not satisfied in the comparative example 1-4, in which no elastic layer is interposed between the base element and the separation layer.

It is further found that an increase in the thickness of the separation layer causes the value of the universal hardness to be increased (hardened) in the case of interposing the elastic layer. The principle of determining the universal hardness has already been described in the above explanation. When this measurement method is applied to the material to be measured in the present invention, in which case, the material comprises the resins and gummy materials, it follows that "the apparent indentation depth measured by an indentation probe"="the actual indented depth of the probe onto the surface"+"the depth corresponding to the bending of the surface".

When, therefore, a separation layer is formed on an elastic layer, a decrease in the thickness of the separation layer causes the flexibility of the elastic layer to be enhanced on the belt surface (the surface of the separation layer), so long as the hardness of the elastic layer<the hardness of the separation layer (it is assumed that this condition generally holds). That is, "the depth corresponding to the bending of the surface" increases and, therefore, it can be recognized that the value of the universal hardness becomes apparently small.

The material PFA No. 1 is less flexible than the material PFA No. 2. Such a difference in the elasticity (flexibility) of the fluorocarbon resin will be explained. The material used for the separation layer is generally selected from such fluorocarbon resins, in which case, the hardness depends on the difference in the type of the resin; FEP, PFA, PTFE or the like, the difference in the molecular weight, the existence/non-existence of a filler, the coating method and/or the like. The hardness is dependent on the grade as for the difference in the type and generally increases with the increase of the molecular weight. Moreover, the hardness is influenced not only by the type of polymer but also the addition of filler.

As a filler, carbon black, whisker, silica, silicone carbide, mica or the like can be used for enhancing the wear resistance, and furthermore carbon black, metal oxide or the like is used for providing the electrical conductivity. The addition of such a filler generally allows the material to be hardened.

As shown in Table 1, the universal hardness becomes different from the material used for the separation layer, when the same structural arrangement (the same layer thickness) is employed. The material PFA No. 1 provides a more restricted allowance for the matt image at an increased layer thickness, compared with the material PFA No. 2. From the results of the present test, it can be recognized that, in order to transfer the elasticity of the elastic layer to the separation layer, the thickness of the separation layer should be specified in accordance with the type of material used for the separation, taking its flexibility into account.

In the comparative example 7, the fixing belt includes a directly exposed elastic layer (silicone gum) without any separation layer and the surface thereof exhibits an extremely small amount of the universal hardness. Nevertheless, the fixing belt is insufficient regarding both the durability and the separation ability. In fact, regarding the durability, the damage resulting from the contact area with a thermistor and/or the edges of a continuously passing recording paper on the surface of the silicone gum appears in the initial stage of evaluation. Regarding the separation ability, the fixable temperature difference between the cold offset and the hot offset is small, in particular for a thin type paper (45 kg paper) used as the recording paper, when a separation layer made of the fluorocarbon resin is employed. It can be stated, therefore, that a separation layer should be formed on the elastic layer.

In order to avoid inconvenience or problem in the matt image (especially in the case of a highly glossy image), it is indispensable to provide an appropriate flexibility to the fixing belt. For this purpose, it is effective to use the universal hardness as a characterization value for evaluating the flexibility. The universal hardness of the surface of the fixing belt depends on the type of the material for the elastic layer and the thickness thereof as well as the type of the material for the separation layer and the thickness thereof. An appropriate combination of these parameters makes it possible to satisfy the conditions for the universal hardness defined by the equations (1) and (2) or the equations (3) and (4), thereby enabling an evenness to be obtained in the gloss (image).

However, as is also seen from the comparative example 7 in Table 1, the exposure of the gum material from the belt surface causes a practical inconvenience to be generated with regard to both the durability and the separation ability, and therefore it is necessary to apply a separation layer made of PTFE, PFA, FEP or a mixture thereof onto the surface of the elastic layer.

If a fluorocarbon resin having a very high flexibility is successfully developed, the structural arrangement without the elastic layer, i.e., the base element+the separation layer is capable of providing the universal hardness within the above-mentioned range. At the present range, however, it appears that such a triple layer structure as the base element+the elastic layer+the separation layer satisfies all of the requirements as for the evenness in the gloss (image), the toner separation ability and the durability.

Second Embodiment

In the following, using fixing belts in which the type of material and the layer thickness as for both the elastic layer and the separation layer are varied (experimental examples 6 to 10), the universal hardness test was carried out for indentation depths of 1 μm, 4 μm and 20 μm at test environment temperatures of 25° C., 60° C., 100° C., 150° C. and 200° C. The test results are summarized in Table 2.

In the experimental examples 6 to 10, the material and the layer thickness of the fixing belts are as follows:

EXPERIMENTAL EXAMPLE 6

Elastic layer: Silicone gum; hardness 25° (JIS K 6301), layer thickness 200 μm,

Separation layer: Type of material, A; layer thickness 15 μm.

EXPERIMENTAL EXAMPLE 7

Elastic layer: Silicone gum; hardness 25° (JIS K 6301), layer thickness 200 µm,

Separation layer: Type of material, B; layer thickness 30 µm,

EXPERIMENTAL EXAMPLE 8

Elastic layer: Silicone gum; hardness 25° (JIS K 6301); layer thickness 200 µm,

Separation layer: Type of material, C; layer thickness 30 µm.

EXPERIMENTAL EXAMPLE 9

Elastic layer: Silicone gum; hardness 25° (JIS K 6301); layer thickness 300 µm,

Separation layer: Type of material, C; layer thickness 10 µm.

EXPERIMENTAL EXAMPLE 10

Elastic layer: Silicone gum; hardness 25° (JIS K 6301); layer thickness 200 µm,

Separation layer: Type of material, D; layer thickness 20 µm.

In the above, each of the types A to D of material uses a fluorocarbon resin including at least one of PTFE, PFA and FEP as basic ingredient. Mechanical strength of the fluorocarbon, such as hardness, elongation or is changed by a kind, a molecular weight and a formed method of the fluorocarbon resin. It is possible to enhance the hardness of fluorocarbon resin by adding a filler such as carbon black, graphite, and, mica therein. Each of the types A to D represents the separation layer in which factors influenced the hardness of the layer. Concretely, the type A is a mixture of PTFE/PFA, the type B is a material added carbon black in PFA, the type C is a low molecular weight material, for example, PFA and the type D is a high molecular weight material, for example, PFA.

In Table 2, the following data are listed: (A) data for an indentation depth of 1 µm; (B) data for an indentation depth of 4 µm; (C) data for an indentation depth of 20 µm; and (D) data averaged over the values for the indentation depths of 1 µm, 4 µm and 20 µm.

Figure 10A:
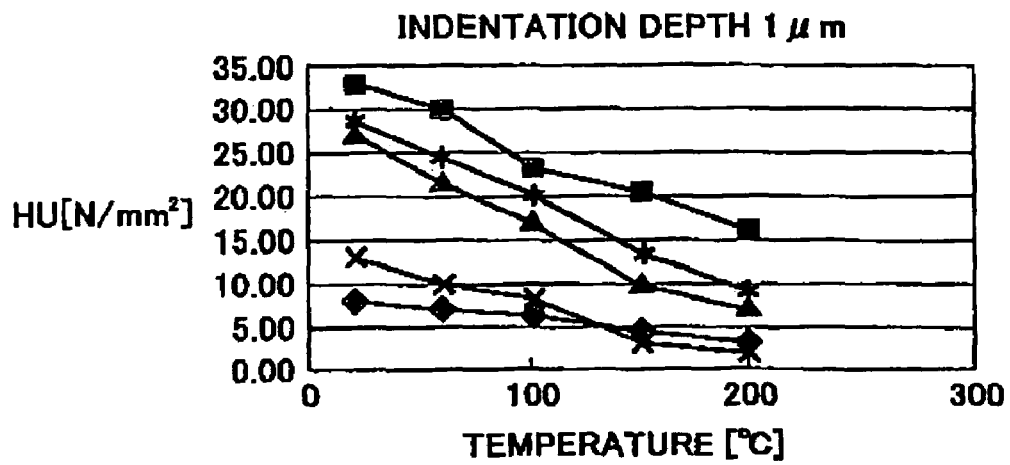
FIG. 10A is a diagram showing a relationship between the universal hardness and the test environment temperature at an indentation depth=1 μm.
Figure 10B:
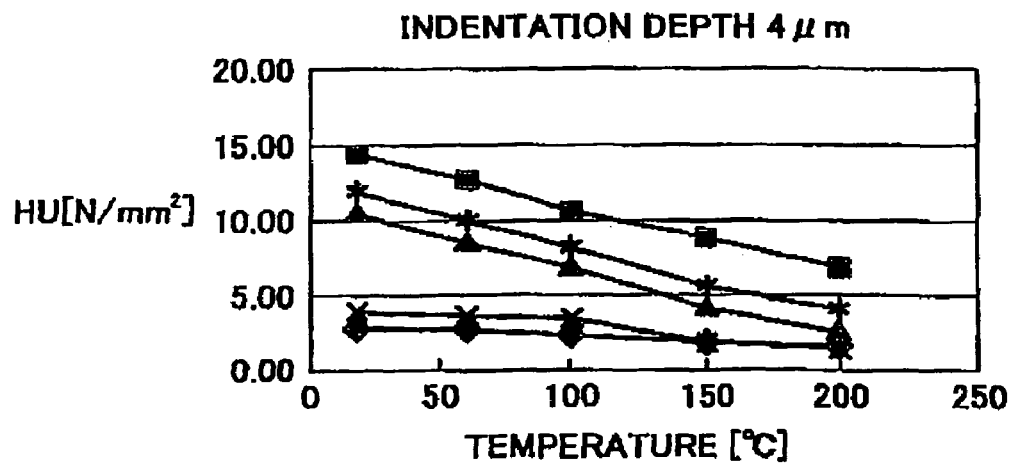
FIG. 10B is a diagram showing a relationship between the universal hardness and the test environment temperature at an indentation depth=4 μm.
Figure 10C:
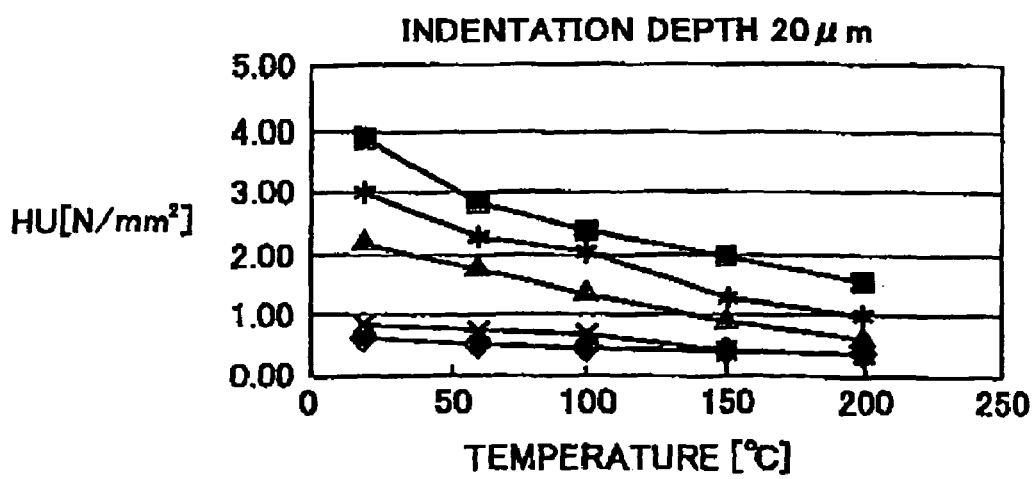
FIG. 10C is a diagrams showing a relationship between the universal hardness and the test environment temperature at an indentation depth=20 μm.

In addition, the data in Table 2 provide diagram in FIG. 10, where the abscissa is the test environment temperature and the coordinate is the universal hardness. In FIG. 10 diagram (A) is the data for the indentation depth of 1 µm; diagram (B) is the data for the indentation depth of 4 µm; and diagram (C) is the data for the indentation depth of 20 µm. FIG. 11 is the diagram obtained by averaging the data at each of the indentation depths of 1 µm, 4 µm, and 20 µm.

From the diagrams in FIGS. 10 and 11, it can be recognized that an increase in the test environment temperature causes the universal hardness to be decreased, and in particular, such a trend becomes more prominent in the indentation depth of 1 µm.

Figure 13:
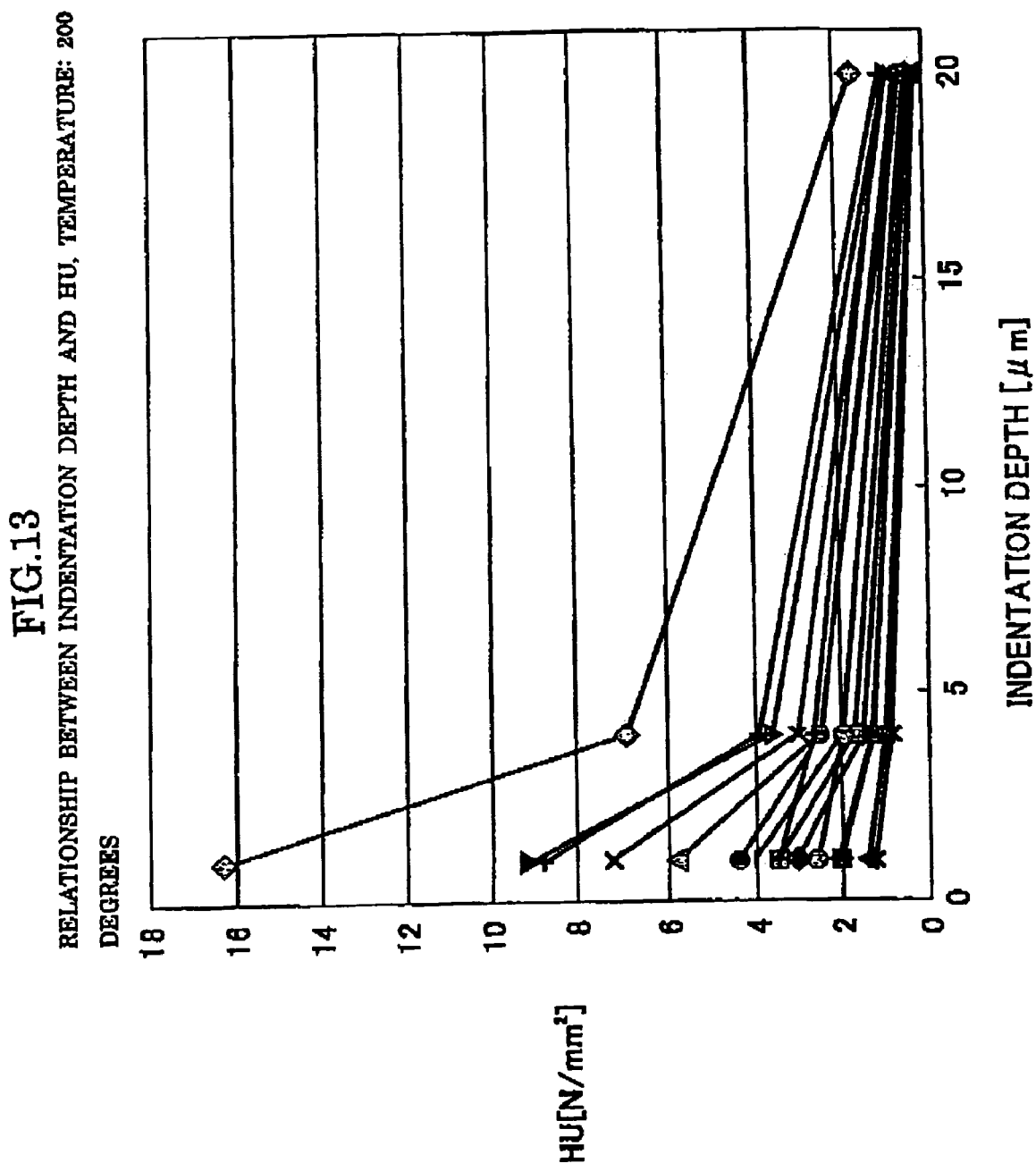
FIG. 13 is a diagram showing a relationship between the universal hardness and the indentation depth.

Furthermore, providing 12 fixing belts other than the firing belts used in the experimental examples 6 to 10, the universal hardness test for each of these fixing belts was carried out at test environment temperature of 25° C. and 200° C. and for indentation depths of 1 µm, 4 µm and 20 µm. The results of this test are shown in FIGS. 10 and 11, along with those in examples 6 to 10. In the diagrams of FIGS. 12 and 13, the abscissa and the coordinate mean the indentation depth and the universal hardness, respectively. FIG. 12 depicts a diagram of experimental results at the test environment temperature of 25° C. and FIG. 13 depicts a diagram of experimental results at the test environment temperature of 200° C.

From the diagrams in FIGS. 12 and 13, it can be recognized that, for the indentation depth from 1 µm to 4 µm, the flexibility and the elasticity of both the separation layer and the elastic layer contributes to the universal hardness and therefore an increase in the indentation depth causes the universal hardness to be drastically decreased, whereas for the indentation depth of greater than 4 µm, the contribution mainly results from the base element, thereby causing the universal hardness to be not largely decreased.

In view of these facts, it can be stated that the universal hardness test should be carried out within a range of the indentation depths from 1 µm to 4 µm in order to accurately measure the surface hardness of the fixing belt (or the thermal fixing roller).

The abovementioned data in the experimental examples are represented in FIGS. 14 to 19, similarly to FIGS. 6 to 9; in which case, the abscissa and the coordinate mean the universal hardness and the rank of matt pattern, respectively. In FIGS. 14 to 19, the relationship between the universal hardness and the rank of the matt pattern is represented by a linear equation which is determined by the least squares method, and further correlation coefficient is also determined therefrom. FIGS. 14 to 19 show the results obtained in the case of using the toner No. 2.

Figure 14:
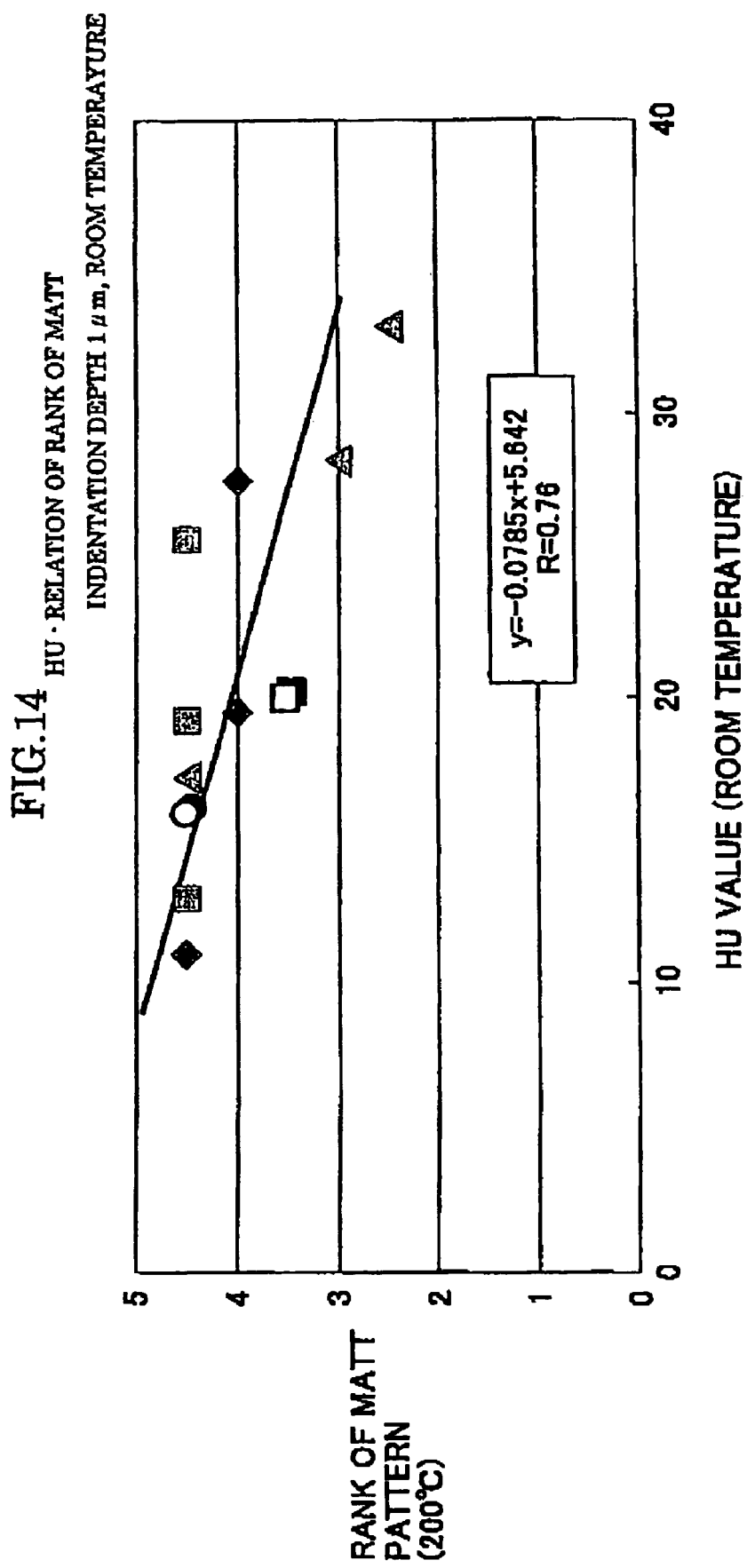
FIG. 14 is a diagram showing a relationship between the universal hardness and the rank of matt pattern.
Figure 15:
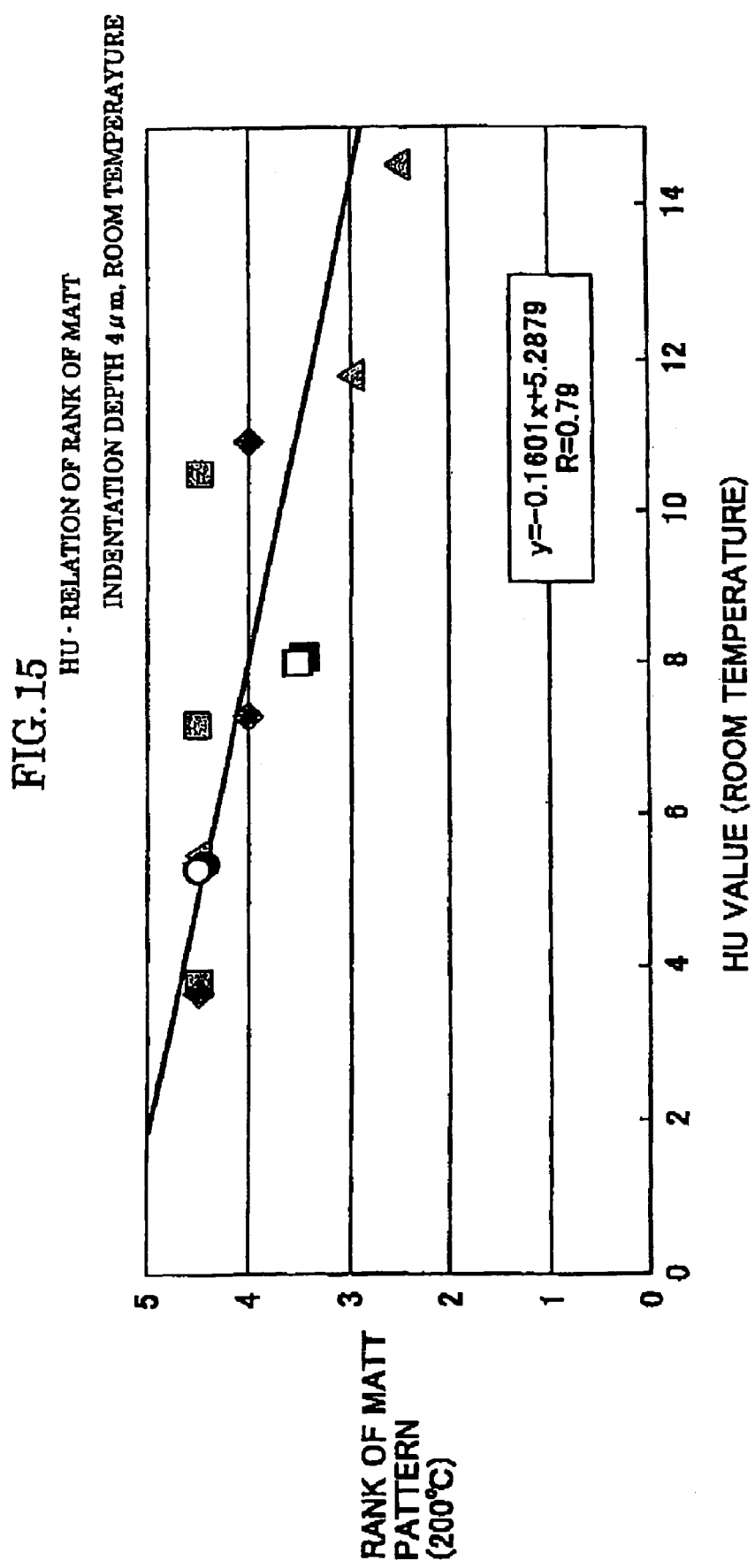
FIG. 15 is a diagram showing a relationship between the universal hardness and the rank of matt pattern.
Figure 16:
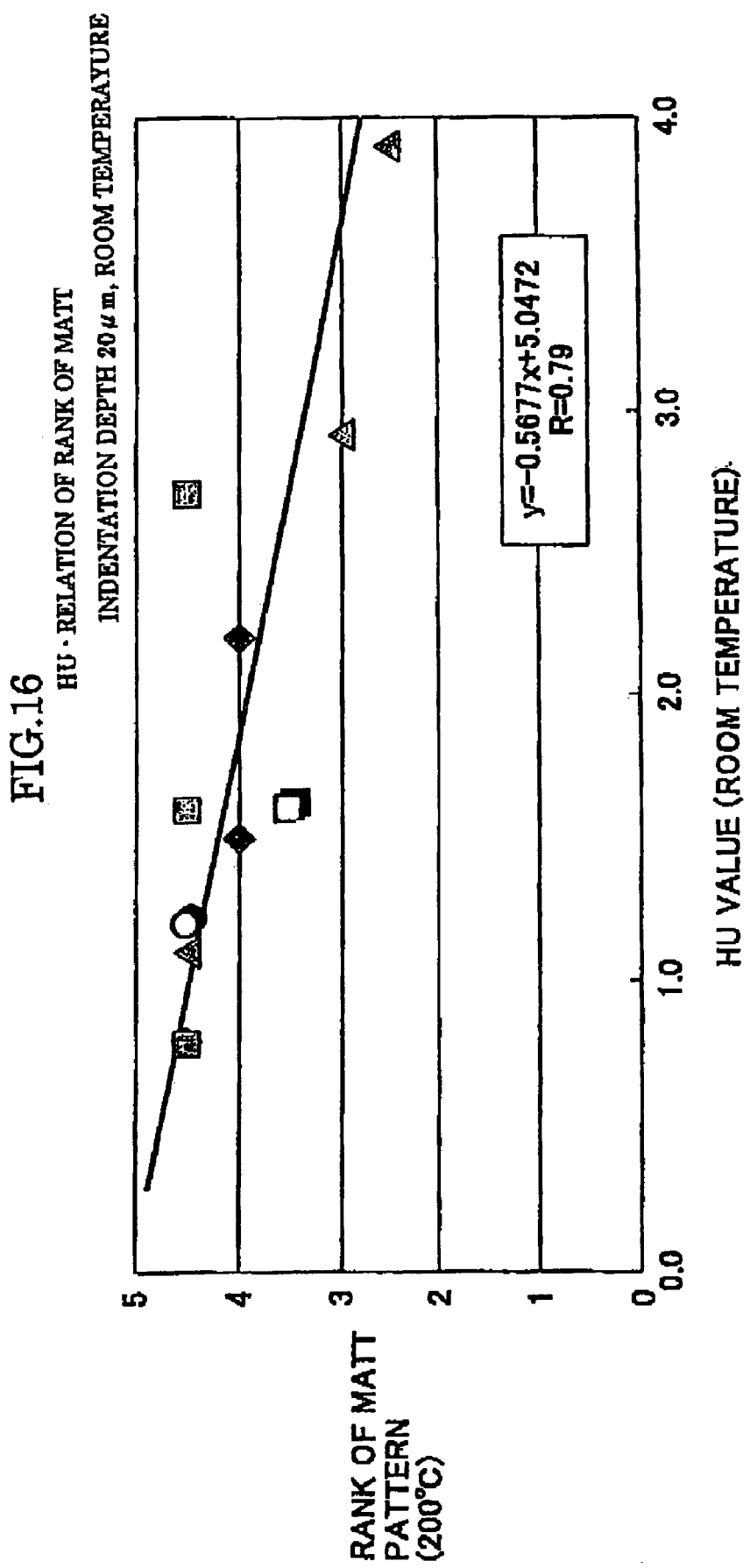
FIG. 16 is a diagram showing a relationship between the universal hardness and the rank of matt pattern.
Figure 17:
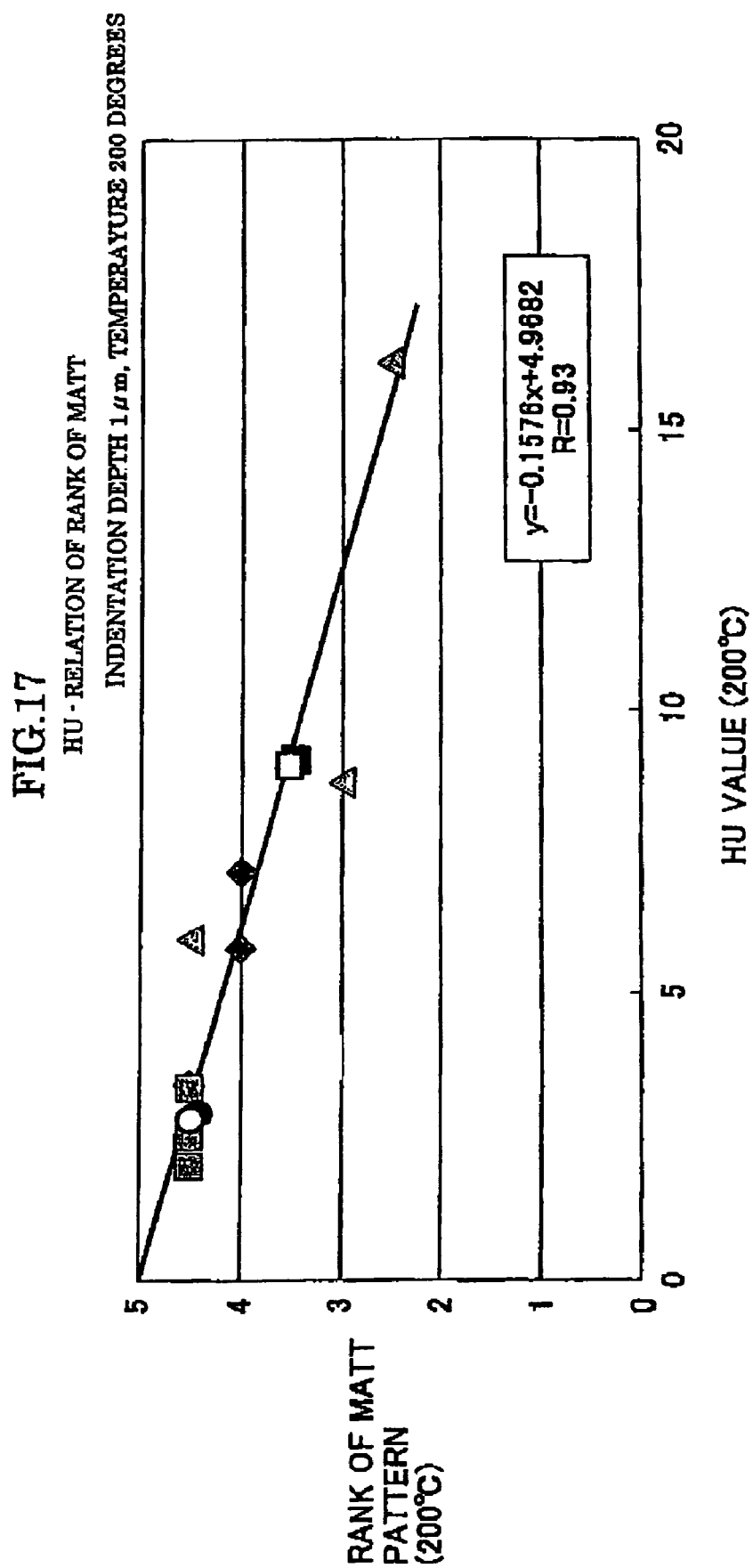
FIG. 17 is a diagram showing a relationship between the universal hardness and the rank of matt pattern.
Figure 18:
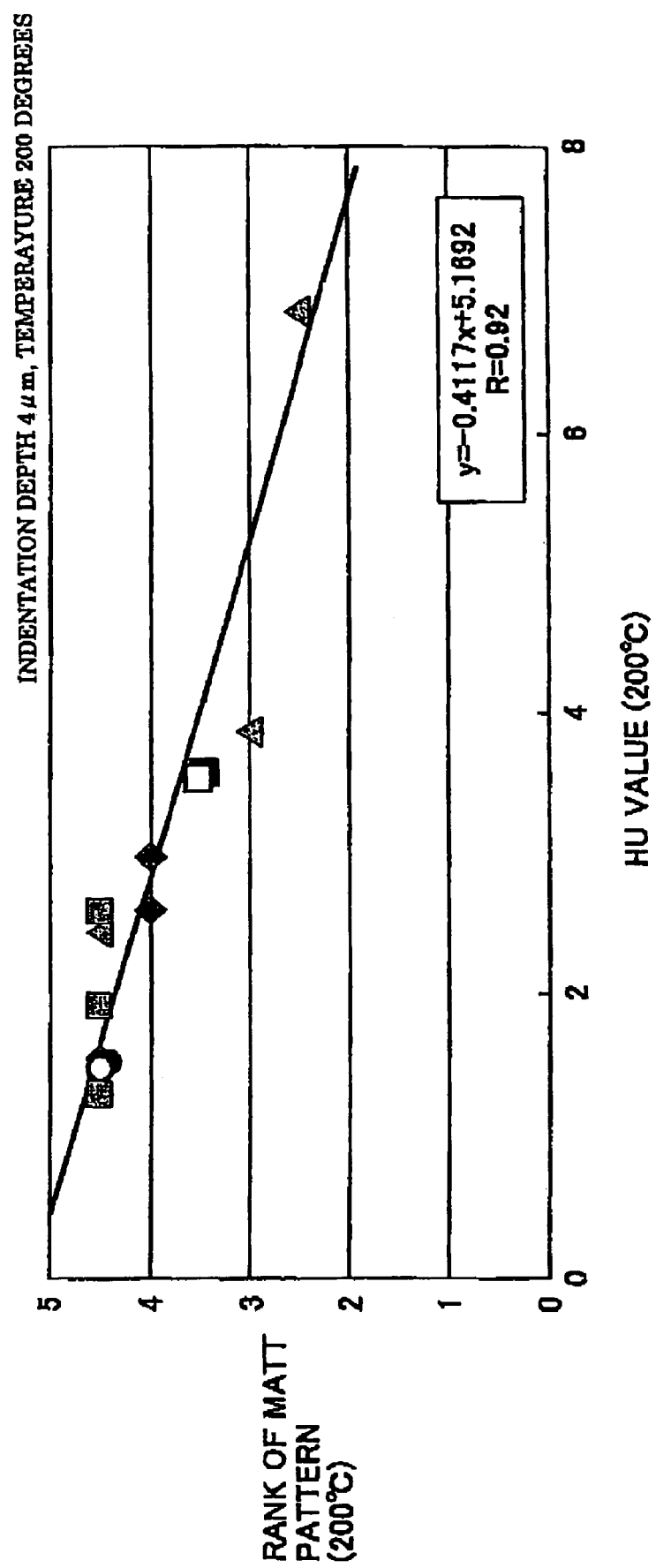
FIG. 18 is a diagram showing a relationship between the universal hardness and the rank of matt pattern.
Figure 19:
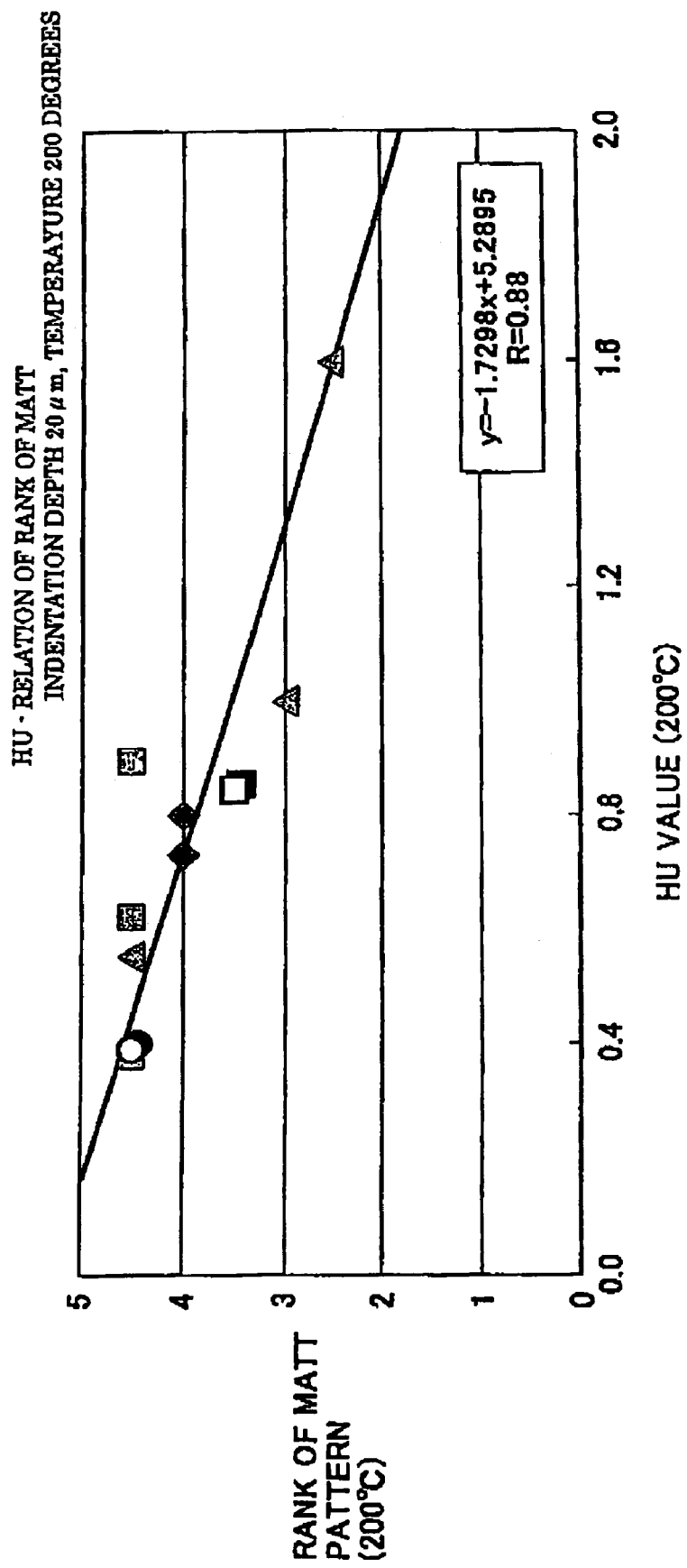
FIG. 19 is a diagram showing a relationship between the universal hardness and a rank of a matt pattern.

FIG. 14 shows the result obtained for an indentation depth 1 µm at room temperature; FIG. 15 shows the result obtained for an indentation depth 4 µm at room temperature; FIG. 16 shows the result obtained for an indentation depth 20 µm at room temperature; FIG. 17 shows the result obtained for an indentation depth of 1 µm at a test environment temperature of 200° C.; FIG. 18 shows the result obtained for an indentation depth of 4 µm at a test environment temperature of 200° C.; and FIG. 19 shows the result obtained for an indentation depth of 20 µm at a test environment temperature of 200° C. The correlation coefficients determined from the diagrams in FIGS. 14 to 19 are listed in Table 3.

Table 3A shows data at the test environmental temperature of 200° C. Table 3B shows data at room temperature.

Third Embodiment

In the fixing condition of the existing copying machine (for instance, RICOH CO. Ltd.: Imagio color 3100), the actual characteristics such as the image quality, the durability, the separation ability or the like are examined. These actual characteristics are strongly affected by the toner and the fixing condition. For example, the durability is affected by the copying (printing) speed, the existence or non-existence of the separation pawl, the pressure of the nip portion or the like. Moreover, the separation ability is strongly affected by the toner. That is, in the above-mentioned evaluation results, regarding to the durability and the separation ability, the required value is changed in accordance with the specification of the copying machine and the printer, which are assumed to be used.

More specifically, the structure of the member or the material having a low durability is allowed for the machine which has a low speed and a short operating life of the machine. Moreover, when the machine having a high accuracy for controlling the temperature (when this kind of machine is used, a narrow range of the fixable temperature is allowed) or the toner having a high separation ability is used, a little decrease in the separation ability of the surface of the member for fixing is allowed. The following investigation was carried out for the structure of the member and the material when these machines having the low specification are used.

(The Evaluation of the Separation Ability)

The separation ability was evaluated by utilizing the above-mentioned copying machine and the toner No. 2. For the silicone gum, various grades of the silicone gums are supplied from a material manufacturer. Lubrication agent and separation agent can be added in the silicone gum. In the present embodiment, the separation ability was evaluated by the contact angle when water-drop is contacted onto the surface of the fixing member and the toner separation ability for the actual machine.

Table 4 shows the relationship between the separation ability and the contact angle when the water-drop is contacted onto the surface of the fixing member, i.e., the contact angle of the material of the surface of the member. In the table, ○ shows the case that the separation ability is the same as using the PFA material. X shows the case that the range of the fixable temperature range is not obtained. Δ shows the case between the ○ and X.

It is recognized that the range of the fixing temperature is obtained if the material can comprise more than 95 degree of the contact angle. According to the result, even though the durability of the fixing member is not high, it is found that the fixing member, which uses the appropriate silicone gum on the surface of the fixing member without using the fluorocarbon resin as the separation layer, has the possibility to be used as the fixing device.

Moreover, the fixing member, which has sufficient flexibility (i.e., the universal hardness HU satisfies the equations (1) and (2) under the measurement in 25° C. of the test environment temperature, and the formulas (3) and (4) under the measurement in 200° C. of the test environment temperature) and the fluorocarbon resin having 95° C. of the contact angle is used as the fixing device without forming the elastic layer.

(The Evaluation of the Durability)

Figure 20:
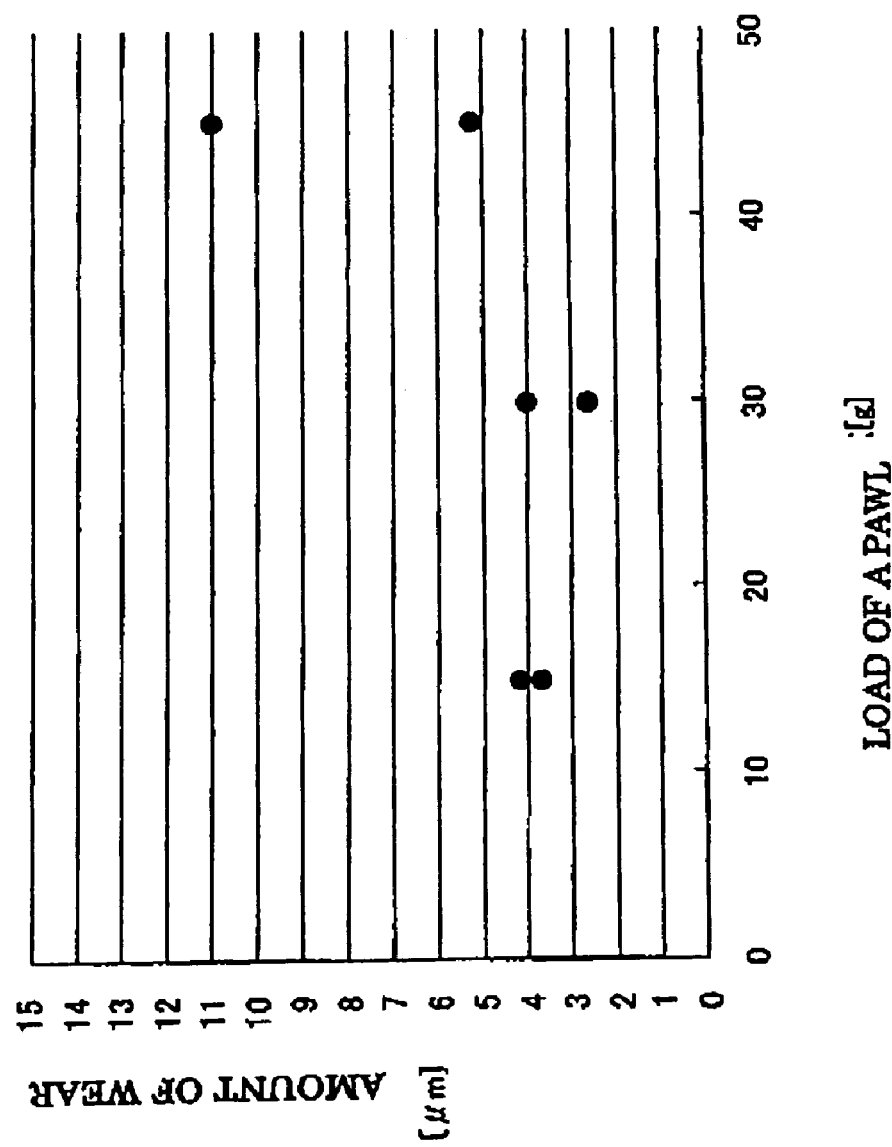
FIG. 20 is a diagram showing a relationship between an amount of wear and a load of a pawl.
Figure 21:
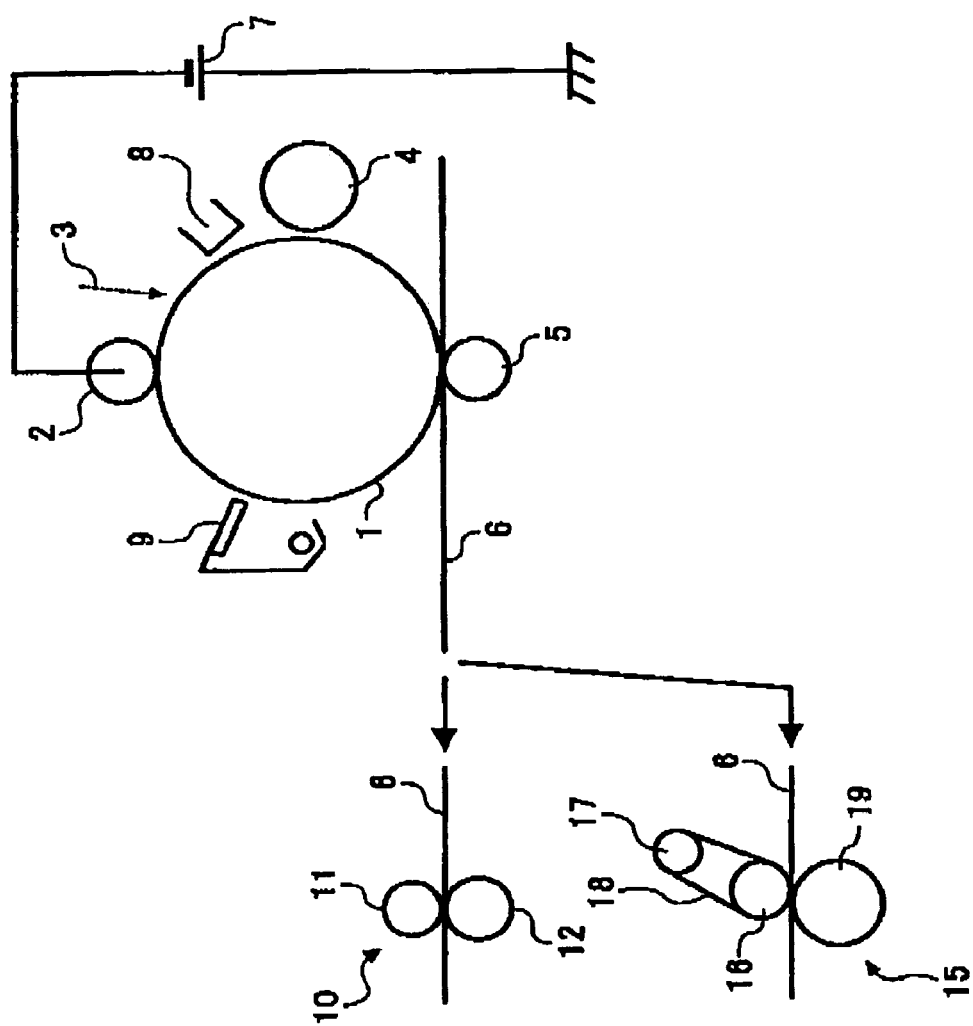
FIG. 21 is a schematic sectional view of an image forming apparatus.

The thermistor, the separation pawl and so on are contacted onto the surface of the fixing belt. FIG. 20 shows the result of the investigation for the amount of the wear caused by the thermistor, the separation pawl and so on.

At this point, a single testing machine for measuring a wear amount of a pawl is used as a device for evaluation. Furthermore, a thermal fixing roller including a 200 μm of the elastic layer and PFA No. 2 of the separation layer, which is inferior to a heat resistance, is used as the fixing member. The amount of the wear on the surface of the thermal fixing roller is measured when about 100000 papers are fed through the thermal fixing roller. The amount of the wear is measured by a profile of a roughness gauge of profilometer.

The load of the pawl is changed in accordance with the fixing condition and the line speed. However, in order to obtain the stable separation performance, about 15 kg of the load is required. The thickness of the separation layer should be more than 5 μm because about 4 μm of separation layer is worn when the load of the pawl is low.

In accordance with the above-mentioned investigations, an excellent quality in an image characteristic (uniformity of image) is obtained in such a manner that the universal hardness HU of a surface of material satisfies ranges of (1) and (2), or ranges of (3) and (4). Regarding the separation ability and the durability, a demanded characteristic is changed by a copying machine, a specification of a printer, and a useable toner. A relatively high separation ability and durability are required for a middle speed machine and a high speed machine (a machine of a high specification), so that it is preferable for the structural arrangement, which had the separation layer onto the elastic layer. However, a single elastic layer or a single separation layer is able to be used respectively in a low speed machine (a machine of a low specification).

As described above, the present invention provides the method for evaluating the fixing member in which the excellence in the toner separation ability, the flexibility, and the elasticity can be easily evaluated, so that the excellent quality of the image without the unevenness of the image is able to be obtained in such a manner that the excellent quality of fixing member is disposed in the thermal fixing apparatus or the image forming apparatus.

The fixing belt and the filing roller, which are effective in the toner separation ability, the flexibility, and the elasticity, can be obtained.

Using the silicone gum as the elastic layer also provides the stable thickness of the layer and the smoothed surface.

The sufficient separation ability and the durability are also ensured by including a material at least one of PTFE, PFA, and FEP.

TABLE 1

| | Separation Layer | | Elastic Layer | Universal Hardness (25° C., Environment) [N/mm$^2$] | | Universal Hardness (200° C., Environment) [N/mm$^2$] | | | |
|---|---|---|---|---|---|---|---|---|---|
| | Material | Layer Thickness [μm] | Layer Thickness [μm] | Indentation Depth 1 μm | Indentation Depth 4 μm | Indentation Depth 1 μm | Indentation Depth 4 μm | Durability | Separation Ability |
| Comparative Example 1 | PFA1 | 20 | No Data | 48.0 | 21.7 | 15.1 | 6.1 | ○ | ○ |
| Comparative Example 2 | PFA2 | 10 | No Data | 46.7 | 21.1 | 12.0 | 6.0 | ○ | ○ |
| Comparative Example 3 | PFA2 | 20 | No Data | 41.1 | 18.2 | 9.1 | 3.9 | ○ | ○ |
| Comparative Example 4 | FEP | 20 | No Data | 46.7 | 21.1 | 9.2 | 4.0 | Δ | ○ |
| Experimental Example 1 | PFA1 | 10 | 200 | 17.2 | 5.5 | 6.0 | 2.5 | ○ | ○ |
| Experimental Example 2 | PFA1 | 20 | 200 | 20.0 | 6.0 | 9.1 | 3.6 | ○ | ○ |
| Comparative Example 5 | PFA1 | 30 | 200 | 33.0 | 14.5 | 16.3 | 6.9 | ○ | ○ |

TABLE 1-continued

| | Separation Layer | | Elastic Layer | Universal Hardness (25° C., Environment) [N/mm$^2$] | | Universal Hardness (200° C., Environment) [N/mm$^2$] | | | |
|---|---|---|---|---|---|---|---|---|---|
| | Material | Layer Thickness [μm] | Thickness [μm] | Indentation Depth 1 μm | Indentation Depth 4 μm | Indentation Depth 1 μm | Indentation Depth 4 μm | Durability | Separation Ability |
| Experimental Example 3 | PFA2 | 10 | 200 | 11.0 | 3.7 | 3.5 | 1.5 | ○ | ○ |
| Experimental Example 4 | PFA2 | 20 | 200 | 19.5 | 7.3 | 5.9 | 2.6 | ○ | ○ |
| Experimental Example 5 | PFA2 | 30 | 200 | 27.5 | 10.9 | 7.2 | 3.0 | ○ | ○ |
| Comparative Example 6 | PFA2 | 40 | 200 | 35.5 | 14.4 | 8.0 | 3.2 | ○ | ○ |
| Comparative Example 7 | — | — | 200 | 0.2 | 0.2 | 0.1 | 0.1 | X | X |

TABLE 2

| | Temperature | | | | |
|---|---|---|---|---|---|
| | 25° C. 20 | 60° C. 60 | 100° C. 100 | 150° C. 150 | 200° C. 200 |
| (a) Indentation Depth 1 μm | | | | | |
| Experimental Example 6 | 7.90 | 7.00 | 6.20 | 4.40 | 3.00 |
| Experimental Example 7 | 33.00 | 30.30 | 23.20 | 20.60 | 16.30 |
| Experimental Example 8 | 27.50 | 21.70 | 17.70 | 9.90 | 7.20 |
| Experimental Example 9 | 13.00 | 10.00 | 7.95 | 3.20 | 2.03 |
| Experimental Example 10 | 28.30 | 24.50 | 20.00 | 13.50 | 8.80 |
| Averaged | 21.94 | 18.70 | 15.01 | 10.30 | 7.47 |
| (σ) | 10.85 | 9.87 | 7.53 | 7.07 | 5.69 |
| (b) Indentation Depth 4 μm | | | | | |
| Experimental Example 6 | 2.72 | 2.52 | 2.32 | 1.85 | 1.45 |
| Experimental Example 7 | 14.50 | 12.80 | 10.50 | 8.80 | 6.90 |
| Experimental Example 8 | 10.90 | 8.90 | 7.00 | 4.30 | 3.00 |
| Experimental Example 9 | 3.80 | 3.50 | 3.40 | 1.80 | 1.30 |
| Experimental Example 10 | 11.80 | 9.80 | 8.20 | 5.50 | 3.90 |
| Averaged | 8.74 | 7.50 | 6.28 | 4.45 | 3.31 |
| (σ) | 5.19 | 4.36 | 3.39 | 2.91 | 2.28 |
| (c) Indentation Depth 20 μm | | | | | |
| Experimental Example 6 | 0.60 | 0.51 | 0.49 | 0.39 | 0.35 |
| Experimental Example 7 | 3.90 | 2.80 | 2.30 | 2.00 | 1.60 |
| Experimental Example 8 | 2.20 | 1.80 | 1.50 | 1.00 | 0.80 |
| Experimental Example 9 | 0.79 | 0.71 | 0.69 | 0.41 | 0.38 |
| Experimental Example 10 | 2.90 | 2.30 | 2.10 | 1.30 | 1.00 |
| Averaged | 2.08 | 1.62 | 1.42 | 1.02 | 0.83 |
| (σ) | 1.40 | 0.99 | 0.81 | 0.67 | 0.51 |

(d)

| | Temperature | | | | |
|---|---|---|---|---|---|
| Indentation Depth | 25° C. 25 | 60° C. 60 | 100° C. 100 | 150° C. 150 | 200° C. 200 |
| 1 μm averaged | 21.94 | 18.7 | 15.01 | 10.3 | 7.466 |
| 4 μm averaged | 8.744 | 7.504 | 6.284 | 4.45 | 3.31 |
| 20 μm averaged | 2.078 | 1.624 | 1.416 | 1.02 | 0.826 |

TABLE 3

(a)

| | Indentation Depth (μm) | | | | |
|---|---|---|---|---|---|
| | 1 | 4 | 12 | 20 | 50 |
| 200° C. HU R = | 0.93 | 0.92 | 0.88 | No Data up to 20 μm | |

(b)

| | Indentation Depth (μm) | | | |
|---|---|---|---|---|
| | 1 | 4 | 20 | 50 |
| Room Temperature HU R = | 0.76 | 0.79 | 0.79 | No Data up to 20 μm |

TABLE 4

| Material for surface member | Contact angle [°] | Separation ability |
|---|---|---|
| Silicone gum 1 | 91 | X |
| Silicone gum 2 | 97.5 | Δ |
| Silicone gum 3 | 99.5 | ○ |
| PFA1 | 105 | ○ |
| PFA2 | 110 | ○ |
| Polyimide | 66 | X |

What is claimed is:

1. A fixing belt used to fix a toner, wherein when a measurement is carried out by measuring a hardness value equal to a pressure applied to a surface of the belt by a probe load divided by an area of indentation as a function of indentation depth measured while the pressure is applied at a test environment temperature of 25° C.,
the hardness value for an indentation depth of 1 μm from the surface of the belt is less than or equal to 30 N/mm$^2$, and
the hardness value for an indentation depth of 4 μm is less than or equal to 12 N/mm$^2$.

2. A fixing belt according to claim 1, wherein a contact angle when a water-drop is contacted onto the surface of said belt is more than 95 degrees.

* * * * *